(12) United States Patent
Korytko et al.

(10) Patent No.: US 7,968,686 B2
(45) Date of Patent: Jun. 28, 2011

(54) GLUCAGON RECEPTOR ANTAGONISTS

(75) Inventors: Andrew Ihor Korytko, Oceanside, CA (US); Rohn Lee Millican, Jr., Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 165 days.

(21) Appl. No.: 12/405,458

(22) Filed: Mar. 17, 2009

(65) Prior Publication Data

US 2009/0252727 A1 Oct. 8, 2009

(51) Int. Cl.
*C07K 16/00* (2006.01)
(52) U.S. Cl. .................. 530/387.1; 424/133.1
(58) Field of Classification Search .................. None
See application file for complete search history.

(56) References Cited

U.S. PATENT DOCUMENTS

| | | | |
|---|---|---|---|
| 5,770,445 A | 6/1998 | Kindsvogel et al. | |
| 5,776,725 A | 7/1998 | Kindsvogel et al. | |
| 5,919,635 A | 7/1999 | Kindsvogel et al. | |

FOREIGN PATENT DOCUMENTS

| | | |
|---|---|---|
| EP | 0658200 B1 | 12/2004 |
| WO | WO 02/45494 | 6/2002 |
| WO | WO 03/040309 | 5/2003 |
| WO | WO 2004/096016 | 11/2004 |
| WO | WO 2006/005469 | 1/2006 |
| WO | WO 2008/003641 | 1/2008 |
| WO | WO 2008/036341 | 3/2008 |

OTHER PUBLICATIONS

Yan, et al., *J.Pharmacology and Experiemental Therapeutics*, Fully Human Monoclonal Antibodies Antagonizing the Glucagon Receptor Improve Glucose Homeostasis in Mice and Monkeys,vol. 329, No. 1, pp. 102-111 (2009).
Sorensen, et al., *Diabetes*, Immunoneutralization of Endogenous Glucagon Reduces Hepatic Glucose Output and hmproves Long-Term Glycemic Control in Diabetic *ob/ob* Mice, vol. 55, No. 10, pp. 2843-2848 (2006).
Buggy et al., *Horm. Metab. Res.* 28 (1996) 215-219.
Burcelin, et al., *Gene* 164 (1995) 305-310.
Co, et al., *Proc. Natl. Acad. Sci. USA* 88, 2869 (1991).
D'Orazio et al., *Clin. Chem. Lab. Med.* 44(12): 1486-1490 (2006).
Etgen et al., *Metabolism* 49(5): 684-688 (2000).
Isaacs et al., *Clin. Exp. Immunol.* 106:427-433 (1996).
Jones et al., *Nature*, 321:522 (1986).
Kabat, et al., *Ann. NY Acad. Sci.* 190:382-93 (1971).
Konno, et al., *Horm Metab Res.* 37(2):79-83 (Feb. 2005).
McNally et al., *Peptides* 25 (2004) 1171-1178.
Riechmann et al., *Nature*, 332:323-327 (1988).
Unson et al., *PNAS*, 93:310-315, Jan. 1996.
Verhoeyen et al., *Science*, 239:1534 (1988).
Wright et al., *Acta Cryst.* (2000) D56:573-580.
Wu et al., *J. Mol. Biol.*, 294:151-162 (1999).
Cohen, *Bioorg. Med. Chem.*, "Direct observation (NMR) of the efficacy of glucagon receptor antagonists in murine liver expressing the human glucagon receptor," 14:1506-1517(2006).
Dallas-Yang, et al., "Hepatic glucagon receptor binding and glucose-lowering in vivo by peptidyl and non-peptidyl glucagon receptor antagonists," *Eur. J. Pharm.*, 501: 225-234 (2004).
Gelling, et al., "Lower blood glucose, hyperglucagonemia, and pancreatic α cell hyperplasia in glucagon receptor knockout mice," *Proc. Natl. Acad. Sci. USA*, 100:1438-1443 (2003).
Iwanij, et al., "Characterization of the Glucagon Receptor and Its Functional Domains Using Monoclonal Antibodies," *J. Biol. Chem.*, 265(34):21302-21308 (1990).
Liang, et al., "Reduction in Glucagon Receptor Expression by an Antisense Oligonucleotide Ameliorates Diabetic Syndrome in *db/db* Mice," *Diabetes*, 53:410-417 (2004).
Parker, et al., "Glycemic Control in Mice with Targeted Disruption of the Glucagon Receptor Gene," *Biochem. Biophys. Res. Commun.*, 290:839-843 (2002).
Sloop, et al., "Hepatic and glucagon-like peptide-1-mediated reversal of diabetes by glucagon receptor antisense oligonucleotide inhibitors," *J. Clin. Invest.*, 113:1571-1581 (2004).
Sorensen, et al., "Glucagon Receptor Knockout Mice Display Increased Insulin Sensitivity and Impaired β-Cell Function," *Diabetes*, 55:3463-3469 (2006).
Vincent, et al., *J. Cell. Biol.*, 107(6):65A, part 3 (1988).

*Primary Examiner* — Laura B Goddard
*Assistant Examiner* — Meera Natarajan
(74) *Attorney, Agent, or Firm* — Sanjay M. Jivraj; Andrea M. Castetter

(57) ABSTRACT

The present invention relates to glucagon receptor polypeptide antagonists which inhibit the binding of the hormone glucagon to its receptor. More particularly, the present invention relates to high affinity glucagon receptor antibodies or Fab fragments thereof that inhibit binding of glucagon to its receptor and their use in the treatment or prevention of type 2 diabetes (NIDDM) and related disorders in mammalian species.

4 Claims, No Drawings

GLUCAGON RECEPTOR ANTAGONISTS

FIELD OF THE INVENTION

The present invention relates to glucagon receptor polypeptide antagonists which inhibit the binding of the hormone glucagon to its receptor. More particularly, the present invention relates to high affinity glucagon receptor antibodies or Fab fragments thereof that inhibit binding of glucagon to its receptor and their use in the treatment or prevention of type 2 diabetes (NIDDM) and related disorders in mammalian species.

BACKGROUND TO THE INVENTION

Glucagon is 29 amino acid peptide hormone produced by pancreatic α-cells in response to low blood glucose levels. Glucagon binds to a membrane-associated glucagon receptor on the surface of hepatocytes, which triggers a G-protein signal transduction cascade, activating intracellular cyclic AMP and leading to release of glucose through denovo synthesis (gluconeogenesis) and glycogen breakdown (glycogenolysis).

Unson et al., disclose polyclonal antibodies raised against synthetic peptides corresponding to two extracellular portions of the rat receptor. In the assay disclosed, polyclonal antibodies raised against amino acid residues 126-137 and 206-219 were found to block binding of glucagon to the receptor in rat liver membranes (Unson et al., PNAS Vol. 93, pp. 310-315, January 1996).

Buggy et al., discloses the preparation of a monoclonal antibody that is said to compete with glucagon for the hormone binding site of the receptor in an in vitro assay (Buggy et al., Horm. Metab. Res. 28 (1996) 215-219). In the assay disclosed the antibody, given the designation CIV395.7A, recognizes the human and rat glucagon receptors, but not mouse. In order to develop antibodies for human therapeutic treatments it is commonly necessary to perform pre-clinical efficacy and safety studies in validated rat and/or murine animal models. It would therefore greatly facilitate drug development of a therapeutic antibody and thus be highly desirable to provide a pre-clinical therapeutic antibody candidates that are able to bind rat, murine and human forms of the glucagon receptor.

Wright et al., disclose a monoclonal antibody designated hGR-2 F6 and the amino acid sequence of a Fab fragment thereof. This antibody has been raised in a mouse against the human glucagon receptor and described in the disclosed assay as a competitive antagonist at this receptor (Wright et al., Acta Cryst. (2000) D56, 573-580). The applicant has found that hGR-2 F6 binds to the rat and murine forms of the glucagon receptor with only low affinity, and no therapeutic efficacy has been found for hGR-2F6 in a diabetic rat in vivo model at high doses. In particular, this antibody was unable to reduce blood serum glucose in the rat model with any statistical significance (unpublished).

The applicant has identified a need to provide therapeutic monoclonal antibodies that will bind with high affinity to the glucagon receptor and thereby inhibit the binding of glucagon thereto, to provide effective treatments for diabetes, preferably type 2 diabetes and related disorders. Furthermore, in order to allow pre-clinical drug development of an antibody it is clearly desirable to provide monoclonal antibodies that can bind to the human, rat and murine forms of the glucagon receptor to allow obligatory pre-clinical safety and efficacy studies to be undertaken.

SUMMARY OF INVENTION

The present invention relates to novel monoclonal antibodies or Fab fragments thereof that are able to specifically bind with a high affinity to native glucagon receptors of human, rat and murine origin. Furthermore, the present inventors provide monoclonal antibodies or Fab fragments thereof that not only bind glucagon receptors of multiple origins, but for the first time provide glucagon receptor binding monoclonal antibodies that show in vivo efficacy in their ability to reduce blood serum glucose.

In a first aspect the present invention relates to a Fab fragment or humanized monoclonal antibody comprising said Fab fragment, wherein said Fab fragment capable of binding to human, rat and murine glucagon receptors and inhibits glucagon binding to each receptor with a Ki of less than 50 nM.

In a further unexpected finding the inventors for the first time provide antibodies or Fab fragments thereof capable of specifically binding to the glucagon receptor that are able to significantly increase in vivo serum concentrations of GLP-1. Increasing serum levels of GLP-1 is known in the art to enhance β-cell function, reduce glucagon secretion and delay gastric emptying and is recognized as being highly advantageous in the treatment of diabetes type 2 and associated conditions.

In a second aspect, the invention relates to a pharmaceutical composition comprising an effective amount of a Fab fragment or humanized monoclonal antibody according to the present invention and a pharmaceutically acceptable excipient.

In a third aspect, the invention provides a method of treating type 1 or type 2 diabetes and in the achievement of weight loss in a human, wherein said method comprises administrating an effective amount of a Fab fragment or humanized monoclonal antibody according to the present invention, to a patient in need thereof.

A fourth aspect of the invention comprises a Fab fragment or humanized monoclonal antibody according to the present invention for use as a medicament.

A fifth aspect of the invention of relates to the use of a Fab fragment or humanized monoclonal antibody according to the present invention in the manufacture of a medicament for the treatment or prevention of type 1 or type 2 diabetes or in the achievement of weight loss in a human.

DETAILED DESCRIPTION

The present invention relates to a Fab fragment or humanized monoclonal antibody comprising said Fab fragment, wherein said Fab fragment is capable of binding to human, rat and murine glucagon receptors and inhibits glucagon binding to each receptor with a Ki of less than 50 nM.

The invention also provides monoclonal antibodies, which in addition to the glucagon receptors of human, rat and murine origin, are also able to bind with a high affinity to the glucagon receptor of a cynomologous monkey. Preferably, the Fab fragment or humanized monoclonal antibody comprising said Fab fragment therefore also inhibits glucagon binding to a cynomologous monkey glucagon receptor with a Ki of less than 50 nM. Preferably the Fab fragment or humanized monoclonal antibody comprising said Fab fragment has a Ki at each of the named glucagon receptors of less than 30 nM, more preferably less than 20 nM, further preferred less than 10 nM. Further preferred the Fab fragment has an in vitro Ki at the rat, murine and cyno receptors of less than 20 nM and in vitro Ki at the human receptor of less than 5 nM. More preferably the Ki of the Fab fragment, and in particular at the human glucagon receptor, is from 0.1 nM to 15 nM, most preferably from 1 to 10 nM.

A Fab fragment or humanized monoclonal antibody comprising said Fab fragment according to the present invention preferably has a functional binding affinity (Kb) at the human and rat glucagon receptors of at least 100 nM. Further preferred the Fab fragment or humanized monoclonal antibody comprising said Fab fragment has a functional binding affinity at these receptors of at least 50 nM, more preferably at least 10 nM. In a most preferred embodiment the Fab fragment or humanized monoclonal antibody comprising said Fab fragment has a functional binding affinity at the human and rat glucagon receptor of 1 to 10 nM.

In a particularly unexpected finding, the applicant has noted a very rapid rate at which serum GLP-1 is increased and serum blood glucose decreased on in vivo exposure to the Fab fragment or humanized monoclonal antibody comprising said Fab fragment having the binding properties identified in accordance with this invention. In order to maximize this favourable effect it is preferable that the Fab fragment or humanized monoclonal antibody comprising said Fab fragment does not appreciably bind to the GLP receptor i.e. Ki greater than 5000 nM.

Description Of The Sequences

SEQ ID NOS 1 to 22 refer to the light and heavy chain CDRs of Table 1:
SEQ ID NOS 23 to 30 refer to preferred human framework regions described herein:
SEQ ID NOS 31 and 32 are amino acid and cDNA sequences of the human GluR:
SEQ ID NOS 33 and 34 are amino acid and cDNA sequences of the rat GluR:
SEQ ID NOS 35 and 36 are amino acid and cDNA sequences of the murine GluR:
SEQ ID NOS 37 and 38 are amino acid and cDNA sequences of the cyno GluR:
SEQ ID NOS 39 and 40 are the variable region amino acid sequences of example 1 (Ab1)
SEQ ID NOS 41 and 42 are the variable region amino acid sequences of example 2 (Ab2)
SEQ ID NOS 43 and 44 are the variable region amino acid sequences of example 3 (Ab3)
SEQ ID NOS 45 and 46 are the variable region amino acid sequences of example 4 (Ab4)
SEQ ID NOS 45 and 47 are the variable region amino acid sequences of example 5 (Ab5)
SEQ ID NOS 45 and 48 are the variable region amino acid sequences of example 6 (Ab6)
SEQ ID NOS 45 and 49 are the variable region amino acid sequences of example 7 (Ab7)
SEQ ID NO: 50 refers to a preferred kappa light chain IgG4 constant region.
SEQ ID NO: 51 refers to a preferred heavy chain CH1 constant domain.
SEQ ID NO: 52 refers to a preferred modified human IgG4 Fc region.
SEQ ID NOS 53 to 55 refer to preferred light chain CDRs.
SEQ ID NOS 56 to 68 refer to preferred heavy chain CDRs.
SEQ ID NOS 59 and 60 are light and heavy chain protein sequences of example 1 (Ab1).
SEQ ID NOS 61 and 62 are light and heavy chain protein sequences of example 2 (Ab2).
SEQ ID NOS 63 and 64 are light and heavy chain protein sequences of example 3 (Ab3).
SEQ ID NOS 65 and 66 are light and heavy chain protein sequences of example 4 (Ab4).
SEQ ID NOS 65 and 67 are light and heavy chain protein sequences of example 5 (Ab5).
SEQ ID NOS 65 and 68 are light and heavy chain protein sequences of example 6 (Ab6).
SEQ ID NOS 65 and 69 are light and heavy chain protein sequences of example 7 (Ab7).
SEQ ID NOS 70 and 71 are light and heavy chain DNA sequences of example 1 (Ab1).
SEQ ID NOS 72 and 73 are light and heavy chain DNA sequences of example 2 (Ab2).
SEQ ID NOS 74 and 75 are light and heavy chain DNA sequences of example 3 (Ab3).
SEQ ID NOS 76 and 77 are light and heavy chain DNA sequences of example 4 (Ab4).
SEQ ID NOS 76 and 78 are light and heavy chain DNA sequences of example 5 (Ab5).
SEQ ID NOS 76 and 79 are light and heavy chain DNA sequences of example 6 (Ab6).
SEQ ID NOS 76 and 80 are light and heavy chain DNA sequences of example 7 (Ab7).

Definitions

The "glucagon receptor" also referred to herein as "GluR" belongs to the G protein-coupled receptor class 2 family consisting of a long amino terminal extracellular domain, seven transmembrane segments, and an intracellular C-terminal domain. Glucagon receptors are notably expressed on the surface of hepatocytes where they bind to glucagon and transduce the signal provided thereby into the cell. DNA sequences encoding glucagon receptors of rat and human origin have been isolated and disclosed in the art (EP0658200B1). The murine and cynomologous monkey homologues have also been isolated and sequenced (Burcelin, et al., Gene 164 (1995) 305-310); McNally et al., Peptides 25 (2004) 1171-1178).

The term "inhibits" as used herein with respect to an activity of an antibody or Fab fragment thereof of the invention means the ability to substantially antagonize the biological activity of the glucagon receptor. This ability is reflected in the Ki values calculated from the [$^{125}$I] glucagon binding assay described herein.

The term "humanized" as used in reference to a monoclonal antibody of the invention refers to an antibody with at least human frameworks and constant regions (CL, CH domains (e.g., CH1, CH2, CH3), and hinge), and CDRs derived from glucagon receptor binding antibodies. Human frameworks comprise frameworks that correspond to human germline sequences as well as sequences with somatic mutations. Human frameworks and constant regions may be fully human or may vary from the native sequences by one or more amino acid substitutions, terminal and intermediate additions and deletions, and the like. CDRs may be derived from one or more CDRs that bind to the glucagon specific receptors in this application in the context of any antibody framework. For example, the CDRs of the humanized antibody of the present invention may be derived from CDRs that bind glucagon receptors in the context of a mouse antibody framework and then are engineered to bind glucagon receptors in the context of a human framework.

The term "monoclonal antibody" refers to an antibody that is derived from a single copy or clone, including e.g., any eukaryotic, prokaryotic, or phage clone, and not the method by which it is produced. Preferably a monoclonal antibody of the invention exists in a homogeneous or substantially homogeneous population.

The term "in vivo efficacy" as used herein with respect to an antibody of the invention means the ability of the antibody to impart a positive biological effect in a human or animal model. Preferably in vivo efficacy refers to a glucose normalization effect on an animal showing elevated blood glucose in response to an antibody of the present invention as compared to a control response. A diabetic Zucker diabetic fatty rat (ZDF) model (Horm Metab Res. 2005 February; 37(2):79-83) may be appropriately used to assess in vivo efficacy, wherein in vivo efficacy preferably denotes 100% blood glucose normalization on exposure of the animal to $\leq$30 mg/kg dosage of humanized antibody according to the present invention. More preferably in vivo efficacy denotes 100% blood glucose normalization on exposure of the animal to a dosage of $\leq$15 mg/kg of antibody, further preferred at a dosage of $\leq$10 mg/kg, more preferably 0.1 to 5 mg/kg. In a most preferred embodiment in vivo efficacy is used to denote 100% blood glucose normalization in a diabetic ZDF rat model on exposure of the animal to 1 to 3 mg/kg dosage of humanized antibody according to the present invention.

The term "glucose normalization" refers to mean plasma glucose values in a ZDF rat model of less than 120 mg/dL, preferably in the range of 110 to 120 mg/dL. Plasma glucose may be determined in accordance with Etgen et al., (Metabolism 2000; 49(5): 684-688) or calculated from a conversion of whole blood glucose concentration in accordance with D'Orazio et al., (Clin. Chem. Lab. Med. 2006; 44(12): 1486-1490).

As used herein, "Fab fragment" refers to that portion of an antibody molecule, within the variable region, which contains the amino acid residues of the light and heavy chain CDR and framework sequences in addition to CL and CH1 domain.

The 3 CDRs of the heavy chain are herein referred to as "CDRH1, CDRH2, and CDRH3" and the 3 CDRs of the light chain are referred to as "CDRL1, CDRL2 and CDRL3". Assignment of amino acids to each domain is in accordance with a well-known convention (Kabat, et al., *Ann. NY Acad. Sci.* 190:382-93 (1971); Kabat, et al., *Sequences of Proteins of Immunological Interest*, Fifth Edition, U.S. Department of Health and Human Services, NIH Publication No. 91-3242 (1991)). The antigen-binding domain, or the CDRs of the antigen-binding domain, can be derived from other non-human species including, but not limited to, rabbit, mouse, rat or hamster.

The present inventors have identified heavy and light chain CDR sequences which may be used in combination to prepare antibody Fab fragments which demonstrate particularly high affinity for glucagon receptors of murine, rat, cynomologous monkey and human origin. Fab fragments preferably comprise;

(i) a light chain CDRL1: S X S S S V S Y $X_1$ H     SEQ ID NO: 53

(ii) a light chain CDRL2: T T S $X_2$ L A H     SEQ ID NO: 54

(iii) a light chain CDRL3: $X_3$ $X_4$ R S T $X_5$ P P T     SEQ ID NO: 55

(iv) a heavy chain CDRH1: G D D I T S G Y $X_6$ $X_7$     SEQ ID NO: 56

(v) a heavy chain CDRH2: Y I S Y S G S T $X_8$ Y $X_9$ P S L K S     SEQ ID NO: 57

(vi) a heavy chain CDRH3: P P $X_{10}$ Y Y G F G P Y A $X_{11}$ D Y     SEQ ID NO: 58 wherein:

X = Y or A
$X_1$ = M or I
$X_2$ = N or Y
$X_3$ = Q or L
$X_4$ = Q or W
$X_5$ = L or I
$X_6$ = W or H
$X_7$ = N, D or E
$X_8$ = Y, Q, S or V
$X_9$ = N, S or I
$X_{10}$ = G or A
$X_{11}$ = M or L

More preferably, X is Y or A; $X_1$ is I; $X_2$ is Y; $X_3$ is Q or L; $X_4$ is Q or W; $X_5$ is L or I; $X_6$ is W or H; $X_7$ is D or E; $X_8$ is Y, Q, S or V; $X_9$ is S; $X_{10}$ is G or A; $X_{11}$ is L. Further preferred, X is A; $X_1$ is I; $X_2$ is Y; $X_3$ is Q; $X_4$ is Q; $X_5$ is L; $X_6$ is H; $X_7$ is D or E; $X_8$ is Y, Q or S; $X_9$ is S; $X_{10}$ is G or A; $X_{11}$ is L.

Preferably a Fab fragment or humanized monoclonal antibody comprising said Fab fragment of the present invention comprises the CDR sequences:

```
CDRL1   1 2 3 4 5 6 7 8 9 10
        S A S S S V S Y I H

CDRL2   1 2 3 4 5 6 7
        T T S Y L A H

CDRL3   1 2 3 4 5 6 7 8 9
        Q Q R S T L P P T

CDRH1   1 2 3 4 5 6 7 8 9 10
        G D D I T S G Y H D

CDRH2   1 2 3 4 5 6 7 8 9 10 11 12 13 14 15 16
        Y I S Y S G S T Y Y  S  P  S  L  K  S

CDRH3   1 2 3 4 5 6 7 8 9 10 11 12 13 14
        P P G Y Y G F G P Y  A  L  D  Y
``` wherein said Fab fragment has one, two or three amino acid substitutions selected from the group consisting of:
CDRL1: A2Y, I9M;
CDRL2: Y4N;
CDRL3: Q1L, Q2W, L6I;
CDRH1: H9W, D10E, D10N;
CDRH2: Y9Q, Y9S, Y9V, S11N, S11I;
CDRH3: G3A, L12M.

More preferably said Fab fragment comprises one, two or three amino acid substitutions selected from: CDRH1: D10E; CDRH2: Y9Q, Y9S; CDRH3: G3A.

A Fab fragment or humanized monoclonal antibody comprising said Fab fragment according to the present invention preferably comprises CDR sequences selected from:

(i) a light chain with a CDRL1 of SEQ ID NO 2; CDRL2 of SEQ ID NO: 4; CDRL3 of SEQ ID NO: 7; and a heavy chain with a CDRH1 of SEQ ID NO: 1; CDRH2 of SEQ ID NO: 15; CDRH3 of SEQ ID NO: 21;

(ii) a light chain with a CDRL1 of SEQ ID NO 1; CDRL2 of SEQ ID NO: 4; CDRL3 of SEQ ID NO: 6; and a heavy chain with a CDRH1 of SEQ ID NO: 10; CDRH2 of SEQ ID NO: 16; CDRH3 of SEQ ID NO: 20;

(iii) a light chain with a CDRL1 of SEQ ID NO: 3; CDRL2 of SEQ ID NO: 5; CDRL3 of SEQ ID NO: 8; and a heavy chain with a CDRH1 of SEQ ID NO: 1; CDRH2 of SEQ ID NO: 15; CDRH3 of SEQ ID NO: 21;

(iv) a light chain with a CDRL1 of SEQ ID NO 3; CDRL2 of SEQ ID NO: 5; CDRL3 of SEQ ID NO: 6; and a heavy chain with a CDRH1 of SEQ ID NO: 12; CDRH2 of SEQ ID NO: 15; CDRH3 of SEQ ID NO: 21;

(v) a light chain with a CDRL1 of SEQ ID NO 3; CDRL2 of SEQ ID NO: 5; CDRL3 of SEQ ID NO: 6; and a heavy chain with a CDRH1 of SEQ ID NO: 12; CDRH2 of SEQ ID NO: 17; CDRH3 of SEQ ID NO: 21;

(vi) a light chain with a CDRL1 of SEQ ID NO 3; CDRL2 of SEQ ID NO: 5; CDRL3 of SEQ ID NO: 6; and a heavy chain with a CDRH1 of SEQ ID NO: 12; CDRH2 of SEQ ID NO: 15; CDRH3 of SEQ ID NO: 22; and (vii) a light chain with a CDRL1 of SEQ ID NO 3; CDRL2 of SEQ ID NO: 5; CDRL3 of SEQ ID NO: 6; and a heavy chain with a CDRH1 of SEQ ID NO: 13; CDRH2 of SEQ ID NO: 18; CDRH3 of SEQ ID NO: 22.

It is particularly desirable that an antibody in accordance with the present invention shows in vivo efficacy at a low plasma concentration. In vivo efficacy should be observed at a dosage of 30 mg/kg in a ZDF rat model, preferably at a dosage of less than 15 mg/kg, more preferably less than 5 mg/kg, further preferred with the range 0.1 to 5 mg/kg. Most preferably an antibody in accordance with the present invention achieves 100% glucose normalization in a ZDF rat model at a dosage of about 1 to 3 mg/kg. It has been found that particularly preferred antibodies in accordance with the present invention are able to show 100% glucose normalization in an in vivo ZDF rat model at the low dosage of 3 mg/kg. The present invention therefore preferably comprises a Fab fragment or humanized monoclonal antibody comprising said Fab fragment, wherein said Fab fragment comprises:

(i) a light chain with a CDRL1 of SEQ ID NO 3; CDRL2 of SEQ ID NO: 5; CDRL3 of SEQ ID NO: 6; and a heavy chain with a CDRH1 of SEQ ID NO: 12; CDRH2 of SEQ ID NO: 15; CDRH3 of SEQ ID NO: 21;

(ii) a light chain with a CDRL1 of SEQ ID NO 3; CDRL2 of SEQ ID NO: 5; CDRL3 of SEQ ID NO: 6; and a heavy chain with a CDRH1 of SEQ ID NO: 12; CDRH2 of SEQ ID NO: 17; CDRH3 of SEQ ID NO: 21;

(iii) a light chain with a CDRL1 of SEQ ID NO 3; CDRL2 of SEQ ID NO: 5; CDRL3 of SEQ ID NO: 6; and a heavy chain with a CDRH1 of SEQ ID NO: 12; CDRH2 of SEQ ID NO: 15; CDRH3 of SEQ ID NO: 22; or (iv) a light chain with a CDRL1 of SEQ ID NO 3; CDRL2 of SEQ ID NO: 5; CDRL3 of SEQ ID NO: 6; and a heavy chain with a CDRH1 of SEQ ID NO: 13; CDRH2 of SEQ ID NO: 18; CDRH3 of SEQ ID NO: 22.

In a further preferred embodiment the present invention relates to a Fab fragment or humanized monoclonal antibody comprising said Fab fragment, wherein said Fab fragment comprises a light chain with a CDRL1 of SEQ ID NO 3; CDRL2 of SEQ ID NO: 5; CDRL3 of SEQ ID NO: 6; and a heavy chain with a CDRH1 of SEQ ID NO: 12; CDRH2 of SEQ ID NO: 17; CDRH3 of SEQ ID NO: 21. It has been found that an antibody comprising Fab fragments in accordance with this embodiment has a particularly advantageous property of maintaining in vivo efficacy over an extended period as compared to other similar antibodies within the genus being described.

A Fab fragment or humanized monoclonal antibody comprising said Fab fragment of the present invention, preferably comprises light and heavy variable chain framework regions of human origin. Moreover, a variety of different human framework sequences may be used singly or in combination as a basis for the humanized immunoglobulins of the present invention. Preferably, the framework regions of the Fab fragment or humanized monoclonal antibody of the invention are of human origin or substantially of human origin (at least 95%, 97% or 99% of human origin). The sequences of framework regions of human origin may be obtained from ImMunoGenetics (IMGT) via their website http://imgt.cines.fr/textes/IMGTindex/FR.html or from *The immunoglobulin Factsbook*, by Marie-Paule Lefranc, Gerard Lefranc, Academic Press 2001, ISBN 012441351. For example, germline light chain frameworks may be selected from the group consisting of: A11, A17, A18, A19, A20, A27, A30, L1, L11, L12, L2, L5, L15 L6, L8, O12, O2, and O8 and germline heavy chain framework regions may be selected from the group consisting of: VH2-5, VH2-26, VH2-70, VH3-20, VH3-72, VHI-46, VH3-9, VH3-66, VH3-74, VH4-31, VH I-18, VH I-69, VI-13-7, VH3-11, VH3-15, VH3-21, VH3-23, VH3-30, VH3-48, VH4-39, VH4-59, and VH5-5I.

The specific antibodies disclosed herein can be used as a template or parent antibody to make additional antibodies of the invention. In one approach the parent antibody CDRs are grafted into a human framework that has a high sequence identity with the parent antibody framework. The sequence identity of the new framework will generally be at least 80%, at least 85%, or at least 90% with the corresponding framework in the parent antibody. This grafting may result in a reduction in binding affinity compared to the parent antibody. If this is the case, the framework can be back-mutated to the parent framework at certain positions based on specific criteria published by Queen et al., [Queen, et al., Proc. Natl. Acad. Sci. USA 88, 2869 (1991)]. Further methods that may be used include, for example, Jones et al., Nature, 321:522 (1986); Riechmann et al., Nature, 332:323-327 (1988); Verhoeyen et al., Science, 239:1534 (1988).

Most preferably the Fab fragment or humanized monoclonal antibody comprising said Fab fragment according to the present invention comprises the following light chain framework (FR) sequences: FR1 SEQ ID NO: 23; FR2 SEQ ID NO: 24; FR3 SEQ ID NO: 25; FR4 SEQ ID NO: 26; and heavy variable chain frameworks sequences: FR5 SEQ ID NO: 27; FR6 SEQ ID NO: 28; FR7 SEQ ID NO: 29; FR8 SEQ ID NO: 30; wherein these are arranged as light chain variable sequence FR1-CDRL1-FR2-CDRL2-FR3-CDRL3-FR4 and heavy chain variable sequence FR5-CDRH1-FR6-CDRH2-FR7-CDRH3-FR8.

The applicant has surprisingly determined that when predicting the in vivo efficacy of a glucagon receptor antagonism antibody through the use of an in vitro competitive glucagon binding assay, that it is the affinity of the Fab fragment that is positively correlated with in vivo efficacy. Conversely, the binding affinity (Ki) of a full antibody to the glucagon receptor is not necessarily a valid predictor of in vivo efficacy. A process of preparing monoclonal antibodies having the favourable properties sought herein, therefore preferably comprises selecting a Fab fragment that binds to each glucagon receptor with a Ki of less than 50 nM in an in vitro competitive glucagon binding assay using heterologously expressed glucagon receptor gene. More preferably said process comprises selecting a Fab fragment that has an in vitro Ki at each of the glucagon receptors of less than 30 nM, more preferably less than 20 nM, further preferred less than 10 nM. More preferably, the Fab fragment is selected by an in vitro Ki at the rat, murine and cyno receptors of less than 20 nM and in vitro Ki at the human receptor of less than 5 nM. More preferably the Ki of the selected Fab fragment, and in particular at the human glucagon receptor, is from 0.1 nM to 15 nM, most preferably from 1 to 10 nM. Fab fragments identified by this process may then be suitably expressed as full antibodies for therapeutic use by techniques commonly known in the art.

It will be appreciated that applying the teaching of the present invention the person skilled in the art may use common techniques e.g. site directed mutagenesis, to substitute amino acids within the specific CDR and framework sequences herein disclosed and in so doing generate further variable region amino acid sequences derived from the sequences herein provided. Up to all 20 alternative naturally occurring amino acids may be introduced at a specific substitution site. The in vitro selection process defined here above may then be suitably used to screen these additional variable region amino acid sequences for Fab fragments having the claimed cross reactivity and in vitro Ki that has been found by the present applicants to be indicative of in vivo efficacy. In this way further Fab fragments are identified that are suitable for preparing a humanized antibody in accordance with the present invention. Preferably the amino acid substitution within the frameworks is restricted to one, two or three positions within one or each of the framework sequences disclosed herein. Preferably amino acid substitution within the CDRs is restricted to one to three positions within one or each CDR, more preferably substitution at one or two amino acid positions within one or each CDR is performed. Further preferred, amino acid substitution is performed at one or two amino acid positions in the CDRs of the heavy chain variable region. Most preferably amino acid substitution is performed at one or two amino acid positions within CDRH2.

A suitable methodology for combining CDR and framework substitutions to prepare alternative antibodies according to the present invention, using an antibody described herein as a parent antibody, is provided in Wu et al., J. Mol. Biol., 294:151-162.

As used herein, the Fc portion of an immunoglobulin refers to the constant region of an antibody from both heavy chains, which associate through non-covalent interactions and disulfide bonds. The Fc portion can include the hinge regions and extend through the CH2 and CH3 domains to the C-terminus of the antibody. The Fc portion can further include one or more glycosylation sites. Monoclonal antibodies of the present invention may have a heavy chain constant region selected from any of the immunoglobulin classes IgA, IgD, IgG, IgM and IgE. Preferably antibodies of the invention contain an Fc portion which is derived from human IgG4 Fc region because of its reduced ability to bind FcγR and complement factors as compared to other IgG sub-types. More preferably, the IgG4 Fc region of an antibody of the present invention contains substitutions that further reduce effector function [Issacs et al., (1996) Clin. Exp. Immunol. 106:427-433]. These may be selected from one or more of the group comprising proline for glutamate at residue 233, alanine or valine for phenylalanine at residue 234 and alanine or glutamate for leucine at residue 235 (EU numbering, Kabat, E. A. et al. (1991) *Sequences of Proteins of Immunological Interest*, 5th Ed. U.S. Dept. of Health and Human Services, Bethesda, Md., NIH Publication no. 91-3242). These residues corresponds to positions 15, 16 and 17 in SEQ ID NO: 52 and positions 235, 236 and 237 of SEQ ID NO: 67. Further, removing the N-linked glycosylation site in the IgG4 Fc region by substituting Ala for Asn at residue 297 (EU numbering) which corresponds to position 79 of SEQ ID NO:52 is another way to ensure that residual effector activity is eliminated in the context of a humanized antibody.

In addition, the IgG4 Fc portion for use with a humanized monoclonal antibody of present invention preferably contains a substitution that stabilizes heavy chain dimer formation and prevents the formation of half-IgG4 Fc chains. This construct consists of serine at position at 228 (EU numbering) being substituted by proline (amino acid residue 10 in SEQ ID NO:52). The C-terminal lysine residue present in the native molecule may also be deleted in the IgG4 derivative Fc portion of the antibodies discussed herein (position 229 of SEQ ID NO:52; deleted lysine referred to as des-K). A most preferred IgG4 Fc portion is provided by amino acids 221 to 448 of SEQ ID NO: 67.

The invention is further directed to an isolated nucleic acid sequence encoding an antibody of the invention; a vector (or vectors) comprising that nucleic acid, optionally operably linked to control sequences recognized by a host cell transformed with the vector; a host cell comprising that vector; a process for producing an antibody or Fab fragment thereof according to the invention comprising culturing the host cell so that the nucleic acid is expressed and, optionally, recovering the antibody from the host cell culture medium.

In another embodiment, the invention provides a pharmaceutical composition comprising the Fab fragment or humanized monoclonal antibody of the invention. The pharmaceutical composition of the invention may further comprise a pharmaceutically acceptable carrier. In said pharmaceutical composition, the Fab fragment or humanized monoclonal antibody of the invention is the active ingredient. Preferably the pharmaceutical composition comprises a homogeneous or substantially homogeneous population of the Fab fragment or humanized monoclonal antibody of the invention. The composition for therapeutic use is sterile and may be lyophilized, optionally supplied with an appropriate diluent.

A further embodiment of the present invention comprises a host cell or cell culture that is a recipient of any isolated polynucleotide of the invention or any recombinant vector(s) comprising a sequence encoding a HCVR, LCVR, monoclonal antibody or Fab fragment of the invention. Host cells include progeny of a single host cell, and the progeny may not necessarily be completely identical (in morphology or in total DNA complement) to the original parent cell due to natural, accidental, or deliberate mutation and/or change. A host cell includes cells transformed, transduced or infected in vivo or in vitro with one or more a recombinant vectors or a polynucleotide expressing a monoclonal antibody of the invention or a light chain or heavy chain thereof. A host cell which comprises a recombinant vector of the invention (either stably incorporated into the host chromosome or not) may also be referred to as a "recombinant host cell". Preferred host cells for use in the invention are CHO cells, NS0 cells, HeLa, SP2/0 cells or COS cells. Additional host cells for use in the invention include plant cells, yeast cells, other mammalian cells and prokaryotic cells.

The invention embodies an article of manufacture comprising a packaging material and a Fab fragment or humanized monoclonal antibody of the invention contained within said packaging material and wherein the packaging material comprises a package insert which indicates that the Fab fragment or humanized monoclonal antibody neutralizes a GluR or decreases the level of GluR activity in the patient.

Biological Assays:

Glucagon Receptor (GlucR) Membrane Preparations

Membrane preparations for binding studies are prepared from 293HEK cells expressing cloned human, mouse, cynomologous monkey or rat glucagon receptor. Each clonal cell line is first grown as a suspension culture and the frozen cell pellet is resuspended in membrane prep buffer consisting of 25 mM Tris, pH 7.5, 1 mM $MgCl_2$, Complete[R] EDTA-free protease inhibitor tablets (Roche Applied Science), and 20 U/ml DNase I (Sigma Chemical Company) at 4° C. The cells are homogenized with a motor-driven Teflon-glass Potter-Elvehjem homogenizer using 25 strokes, followed by centrifugation at 1800×g for 15 minutes at 4° C. The supernatant is collected and the pellet resuspended in membrane prep buffer, rehomogenized and centrifuged. The second supernatant is combined with the first supernatant and recentrifuged at 1800×g for 15 mins to clarify. The clarified supernatant is transferred to high speed tubes and centrifuged at 25000×g for 30 minutes at 4° C. The membrane pellet (P2) is resuspended in the membrane prep buffer (without DNAase), aliquoted, quick frozen on dry ice and stored at −80° C. until needed.

[$^{125}$I]Glucagon Binding by Scintillation Proximity Assay (SPA).

A competitive receptor/ligand binding experiment is adapted to a scintillation proximity assay (SPA) format. Incubations are performed in clear bottom, opaque 96-well microplates. Compound is serially diluted 3-fold in binding buffer consisting of 25 mM Hepes, pH 7.4, 2.5 mM CaCl$_2$, 1 mM MgCl$_2$, 0.1% fatty acid free BSA, 0.003% tween-20 and Complete$^R$ EDTA-free protease inhibitor tablets. P2 membranes (prepared above) are diluted in binding buffer from each receptor preparation, then added to the diluted compound followed by addition of 0.15 mgs of wheat germ agglutinin (WGA) SPA beads (GE Healthcare) previously blocked with 1% fatty acid free BSA, and 0.15 nM [$^{125}$I]-Glucagon (Perkin-Elmer). Plates are sealed with adhesive sealing tape, mixed end over end, and incubated at room temperature for 12 hours. The radioactivity bound to the receptor (in close proximity to the WGA SPA bead) is quantified on a PE Life and Analytical Sciences Trilux Microbeta plate scintillation counter and expressed as counts per minute (CPM). Total binding is determined in the absence of added compound and nonspecific binding is determined by adding 1 uM glucagon (Lilly Research Labs). The final concentration of 1 uM of unlabeled glucagon is capable of completely inhibiting [$^{125}$I]-glucagon binding to background levels.

[$^{125}$I]Glucagon Binding Data Analysis.

Raw CPM data for concentration curves of compound are converted to percent inhibition by subtracting nonspecific binding from the individual CPM values and dividing by the total binding signal, also corrected for nonspecific binding. Data is analyzed using four-parameter (curve maximum, curve minimum, IC$_{50}$, Hill slope) nonlinear regression routines (XLFit version 3.0: Activity Base, IDBS). The equilibrium dissociation constant determined by competitor inhibited radioligand binding, Ki, is calculated from the absolute IC$_{50}$ value based upon the equation [Ki=IC$_{50}$/(1+D/Kd)] where D equals the concentration of radioligand used in the experiment and Kd equals the equilibrium binding affinity constant of [$^{125}$I]glucagon, in the assay for each individual receptor species.

Glucagon-Stimulated cAMP Functional Antagonist Assay.

The functional antagonist activity is determined from the dose-dependent inhibition of increases in intracellular cAMP with a sub-maximal dose of glucagon using the same clonal rat, mouse, cynomologous, and human glucagon receptor-293HEK cell lines. Quantitation of the intracellular cAMP level is done with an Amplified Luminescent Proximity Homogeneous Assay, (Alpha Screen) from Perkin Elmer (6760625R). Briefly, cAMP generated within the cell competes for binding of a biotinylated cAMP-streptavidin coated Donor bead and a coated anti-cAMP antibody Acceptor bead. As the cAMP level within the cell increases, a disruption of the Acceptor bead-biotinlyated cAMP—Donor bead complex occurs. The functional assay is performed in 10 mM Hepes, pH 7.4, with 0.25 mM IBMX in HBSS containing Mg+2 and Ca+2. The clonal glucagon receptor-293HEK cells are suspended at 2500 cells per well and 1 unit/well of biotinylated cAMP from the kit in a total volume of 20 uls. The cells are pre-incubated for 30 minutes at room temperature with 20 uls of either 3-fold serially diluted compounds or of 3-fold serially diluted cAMP for use as a standard curve. The reaction is started by the addition of 20 uls of 300 pM glucagon (3×), a dose sufficient to produce 90% of the maximal intracellular cAMP. After 60 minutes at room temperature in the dark, the reaction is stopped by the addition of 30 uls of lysis buffer made of 1% IGEPAL CA630 (Sigma) and 0.1% fatty-acid free BSA (Gibco) in 10 mM Hepes, pH 7.4 containing 1 unit each of the kit Donor and Acceptor beads per well. The plates are wrapped in foil to protect the Donor and Acceptor beads from light and mixed on Titertek shaker medium speed for 30 secs. After incubation overnight at room temperature, the plates are read on a Packard Fusion™-α Instrument.

Data Analysis for Functional cAMP Activity.

The alpha screen units are converted to pmoles cAMP generated per well based upon the cAMP standard curve. The pmoles cAMP produced in the presence of compound are converted to % of a maximal response with the submaximal dose of glucagon alone. Within each experiment, the concentration of glucagon needed to produce a 50% response in pmoles cAMP is determined. This EC50 concentration is used to normalize results between runs to a Kb where Kb= (EC50 compound)/[1+(pM glucagon used/EC50 in pM for glucagon dose response)]. The data is analyzed using four-parameter (curve maximum, curve minimum, IC$_{50}$, Hill slope) nonlinear regression routines (XLFit version 3.0: Activity Base, IDBS).

EXAMPLES

Antibody examples Ab-1, Ab-2, Ab-3, Ab-4, Ab-5, Ab-6 and Ab-7 are made and purified as known in the art. An appropriate host cell, such as HEK 293 EBNA or CHO, is either transiently or stably transfected with an expression system for secreting antibodies using an optimal predetermined light chain to heavy chain vector ratio or a single vector system encoding both a light chain (set out in SEQ ID NOS: 70, 72, 74, 76) and a heavy chain (set out in SEQ ID NOS: 71, 73, 75, 77, 78, 79, 80). Clarified medium into which the antibody has been secreted is purified using any of many commonly-used techniques. For example, the medium may be conveniently applied to a Protein A or G Sepharose FF column that has been equilibrated with a compatible buffer, such as phosphate buffered saline (pH 7.4). The column is washed to remove nonspecific binding components. The bound antibody is eluted, for example, by pH gradient (such as 0.1 M sodium phosphate buffer pH 6.8 to 0.1 M sodium citrate buffer pH 2.5). Antibody fractions are detected, such as by SDS-PAGE, and then are pooled. Further purification is optional, depending on the intended use. The antibody may be concentrated and/or sterile filtered using common techniques. Soluble aggregate and multimers may be effectively removed by common techniques, including size exclusion, hydrophobic interaction, ion exchange, or hydroxyapatite chromatography. The purity of the antibody after these chromatography steps is greater than 99%. The product may be immediately frozen at −70° C. or may be lyophilized.

Fab expression is achieved in *E. coli* wherein the Fab molecules are secreted into the periplasmic space. The cell wall is disrupted by osmotic shock, and the Fab containing a His tag is purified on an IMAC column.

Table 1 sets out the CDR combinations used in the antibody examples according to the present invention. The full antibody light chain combines the light chain framework sequences interspaced by three light chain CDRs; Framework 1 (SEQ ID NO: 23)-CDRL1-Framework 2 (SEQ ID NO: 24)-CDRL2-Framework 3 (SEQ ID NO: 25)-CDRL3-Framework 4 (SEQ ID NO: 26) and the light chain constant region (SEQ ID NO: 53). The heavy chain framework sequences are interspaced by three heavy chain CDRs Framework 5 (SEQ ID NO: 27)-CDRH1-Framework 6 (SEQ ID NO: 28)-CDRH2-Framework 7 (SEQ ID NO: 29)-CDRH3-Framework 8 (SEQ ID NO: 30) and then the heavy chain CH1 constant region (SEQ ID NO: 51) followed by Fc domain for the Ab, absent in Fab fragment (SEQ ID NO: 52, wherein $X_{10}$=P; $X_{15}$=E; $X_{16}$=A; $X_{17}$=A; $X_{79}$=N; $X_{229}$=is absent).

TABLE 1

| Example | CDRL 1 SEQ ID | CDRL 2 SEQ ID | CDRL 3 SEQ ID | CDRH 1 SEQ ID | CDRH 2 SEQ ID | CDRH 3 SEQ ID |
|---|---|---|---|---|---|---|
| Ab-1 | 2 | 4 | 7 | 11 | 15 | 21 |
| Ab-2 | 1 | 4 | 6 | 10 | 16 | 20 |
| Ab-3 | 3 | 5 | 8 | 11 | 15 | 21 |
| Ab-4 | 3 | 5 | 6 | 12 | 15 | 21 |
| Ab-5 | 3 | 5 | 6 | 12 | 17 | 21 |
| Ab-6 | 3 | 5 | 6 | 12 | 15 | 22 |
| Ab-7 | 3 | 5 | 6 | 13 | 18 | 22 |

Antibody examples 1 through 7 and Fab fragments thereof all inhibit glucagon binding to human, mouse, cynomologous monkey and rat glucagon receptors in the above glucagon receptor binding assay with a Ki of less than 50 nM.

In Vitro Activity of Antibody of Example 4 (Ab4)

TABLE 2

Functional cAMP Antagonism

| Compound | rat GluR Kb (nM) | n | human GluR Kb (nM) | Stdev | n |
|---|---|---|---|---|---|
| Ab4 | 6.85 | 1 | 6.49 | 0.34 | 2 |

This assay demonstrates that at nanomolar concentrations an Ab4 binding to the GluR can block down stream activities of the rat or human glucagon receptor cell line, and reduce cAMP production by the cells.

TABLE 3

In vitro Ki (nM), for full antibody of Example 4 and respective Fab

| Compound | human GlucR | mouse GlucR | rat GlucR | cyno GlucR | human GLP-1 R |
|---|---|---|---|---|---|
| Glucagon | 3.13 | 2.72 | 12.77 | 5.78 | |
| Ab4 | 1.34 | 0.83 | 1.24 | 6.00 | >5000 |
| Fab4 | 2.90 | 2.43 | 3.30 | 9.42 | ND |

This assay demonstrates that in an in vitro glucagon competition binding assay Ab4 binds with high affinity (Ki) to glucagon receptor of human, mouse, rat, cynomologous monkey origin and low affinity to the human GLP-1 receptor.

In Vivo Activity of Antibody of Example 4 (Ab4)

ZDF rats approximately 8 weeks of age and approximately 400 g in weight are dosed with a single subcutaneous injection of antibody according to example 4 (i.e. Ab4) or a human IgG (hIgG4) control. Each treatment group consists of 6 animals. Blood samples are taken for glucose measurements pre-dose and daily for 13 days following a single subcutaneous 3 or 15 mg/kg dose of the Ab4 or 15 mg/kg of a hIgG control. Blood samples for GLP-1 analysis are taken pre-dose and at 2, 4, 6 and 8 days following the 3 or 15 mg/kg subcutaneous dose of the Ab4 or 15 mg/kg of the hIgG control.

TABLE 4

Blood glucose levels following a single 3 or 15 mg/kg subcutaneous dose of Ab4 or 15 mg/kg negative control to ZDF rats.

| Time (days) | Ab4, 3 mg/kg Mean glucose conc. (mg/dL) | S.D. | Ab4, 15 mg/kg Mean glucose conc. (mg/dL) | S.D. | Control (15 mg/kg hIgG) Mean glucose conc. (mg/dL) | S.D. |
|---|---|---|---|---|---|---|
| 0 | 345.3 | 37.8 | 359 | 29.2 | 366.5 | 22.9 |
| 1 | 225.7 | 53.5 | 143.8 | 27.2 | 374.3 | 22.4 |
| 2 | 97.5 | 4.3 | 85.7 | 5.7 | 389.3 | 22.3 |
| 3 | 92.0 | 7.8 | 89.8 | 9.6 | 361 | 51.5 |
| 4 | 103.7 | 20.6 | 90.0 | 14.2 | 381.7 | 69.0 |
| 5 | 105.3 | 8.9 | 97.3 | 5.2 | 400.8 | 62.2 |
| 6 | 108.3 | 13.8 | 99.3 | 10.0 | 401.2 | 61.3 |
| 7 | 113.7 | 7.8 | 97.5 | 12.2 | 451.7 | 45.5 |
| 8 | 135.8 | 15.5 | 104.3 | 11.4 | 452.8* | 33.6 |
| 9 | 151.0 | 21.1 | 109.2 | 7.0 | 394.3 | 40.8 |
| 10 | 149.0 | 9.2 | 103.0 | 15.3 | 418.3 | 33.3 |
| 11 | 159.3 | 28.9 | 106.3 | 10.3 | 410.0 | 34.4 |
| 12 | 151.7 | 29.9 | 108.2 | 9.5 | 417.7 | 58.8 |
| 13 | 218.5 | 88.1 | 114.8 | 11.5 | 443.0 | 48.9 |

There were 6 rats per group for one value (*) where one animal measured AQL therefore n = 5.

TABLE 5

Plasma GLP-1 levels following a single 3 or 15 mg/kg subcutaneous dose of Ab4 or 15 mg/kg negative control to ZDF rats.

| Time (days) | Ab4, 3 mg/kg Mean GLP-1 (pM) | SD | n | Ab4, 15 mg/kg Mean GLP-1 (pM) | SD | n | Control (15 mg/kg hIgG) Mean GLP-1 (pM) | SD | n |
|---|---|---|---|---|---|---|---|---|---|
| 0 | <6 | N.D. | 0 | <6 | N.D. | 0 | <6 | N.D. | 0 |
| 2 | <6 | N.D. | 0 | 10 | 3 | 2 | <6 | N.D. | 0 |
| 4 | 15 | N.D. | 1 | 13 | 3 | 5 | <6 | N.D. | 0 |
| 6 | 21 | 2 | 3 | 29 | 2 | 5 | <6 | N.D. | 0 |
| 8 | 36 | 5 | 3 | 112 | 54 | 6 | <6 | N.D. | 0 |

The average and sd are determined only from those rats that had quantifiable GLP-1 levels and the n denotes the number of animals per group that had quantifiable GLP-1 levels. If no animals had quantifiable GLP-1 levels the result is listed as <6 pM. N.D. signifies the value was not determined.

---

The invention claimed is:

1. A humanized monoclonal antibody that inhibits binding of glucagon to a glucagon receptor, wherein said antibody comprises a light chain and a heavy chain, wherein
   (i) the light chain comprises the CDRL1 of SEQ ID NO: 3, the CDRL2 of SEQ ID NO: 5 and the CDRL3 of SEQ ID NO: 6; and
   (ii) the heavy chain comprises the CDRH1 of SEQ ID NO: 12, the CDRH2 of SEQ ID NO: 17 and the CDRH3 of SEQ ID NO: 21.

2. The humanized monoclonal antibody according to claim 1, wherein said light chain comprises the variable region sequence of SEQ ID NO: 45 and said heavy chain comprises the variable region sequence of SEQ ID NO: 47.

3. A humanized monoclonal antibody according to claim 2, comprising two light chains of SEQ ID NO: 65 and two heavy chains of SEQ ID NO: 67.

4. A pharmaceutical composition comprising an effective amount of a humanized monoclonal antibody according to claim 1 and a pharmaceutically acceptable excipient.

* * * * *

UNITED STATES PATENT AND TRADEMARK OFFICE
CERTIFICATE OF CORRECTION

PATENT NO. : 7,968,686 B2  
APPLICATION NO. : 12/405458  
DATED : June 28, 2011  
INVENTOR(S) : Andrew Ihor Korytko and Rohn Lee Millican, Jr.

Page 1 of 1

It is certified that error appears in the above-identified patent and that said Letters Patent is hereby corrected as shown below:

On the front page of the patent column 1, section 65, under US 2009/0252727 A1 Oct. 8, 2009, please insert -- Related U.S. Application Data -- then add a line and insert -- Provisional application No. 61/039,902, filed on March 27, 2008. --

In Column 1, line 1, under Other Publications, delete "Experiemental" and insert -- Experimental --, therefor In Column 1, line 6, under Other Publications, delete "hmproves" and insert -- Improves --, therefor Signed and Sealed this
Eighteenth Day of October, 2011

David J. Kappos
*Director of the United States Patent and Trademark Office*

SEQUENCE LISTING

<160> NUMBER OF SEQ ID NOS: 80

<210> SEQ ID NO 1
<211> LENGTH: 10
<212> TYPE: PRT
<213> ORGANISM: Artificial sequence
<220> FEATURE:
<223> OTHER INFORMATION: Synthetic sequence: Humanized CDRL 1

<400> SEQUENCE: 1

Ser Tyr Ser Ser Ser Val Ser Tyr Met His
1               5                   10

<210> SEQ ID NO 2
<211> LENGTH: 10
<212> TYPE: PRT
<213> ORGANISM: Artificial sequence
<220> FEATURE:
<223> OTHER INFORMATION: Synthetic sequence: Humanized CDRL 1

<400> SEQUENCE: 2

Ser Ala Ser Ser Ser Val Ser Tyr Met His
1               5                   10

<210> SEQ ID NO 3
<211> LENGTH: 10
<212> TYPE: PRT
<213> ORGANISM: Artificial sequence
<220> FEATURE:
<223> OTHER INFORMATION: Synthetic sequence: Humanized CDRL 1

<400> SEQUENCE: 3

Ser Ala Ser Ser Ser Val Ser Tyr Ile His
1               5                   10

<210> SEQ ID NO 4
<211> LENGTH: 7
<212> TYPE: PRT
<213> ORGANISM: Artificial sequence
<220> FEATURE:
<223> OTHER INFORMATION: Synthetic sequence: Humanized CDRL 2

<400> SEQUENCE: 4

Thr Thr Ser Asn Leu Ala His
1               5

```
<210> SEQ ID NO 5
<211> LENGTH: 7
<212> TYPE: PRT
<213> ORGANISM: Artificial sequence
<220> FEATURE:
<223> OTHER INFORMATION: Synthetic sequence: Humanized CDRL 2

<400> SEQUENCE: 5

Thr Thr Ser Tyr Leu Ala His
1               5

<210> SEQ ID NO 6
<211> LENGTH: 9
<212> TYPE: PRT
<213> ORGANISM: Artificial sequence
<220> FEATURE:
<223> OTHER INFORMATION: Synthetic sequence: Humanized CDRL 3

<400> SEQUENCE: 6

Gln Gln Arg Ser Thr Leu Pro Pro Thr
1               5

<210> SEQ ID NO 7
<211> LENGTH: 9
<212> TYPE: PRT
<213> ORGANISM: Artificial sequence
<220> FEATURE:
<223> OTHER INFORMATION: Synthetic sequence: Humanized CDRL 3

<400> SEQUENCE: 7

Gln Trp Arg Ser Thr Leu Pro Pro Thr
1               5

<210> SEQ ID NO 8
<211> LENGTH: 9
<212> TYPE: PRT
<213> ORGANISM: Artificial sequence
<220> FEATURE:
<223> OTHER INFORMATION: Synthetic sequence: Humanized CDRL 3

<400> SEQUENCE: 8

Leu Gln Arg Ser Thr Leu Pro Pro Thr
1               5

<210> SEQ ID NO 9
<211> LENGTH: 9
<212> TYPE: PRT
<213> ORGANISM: Artificial sequence
<220> FEATURE:
<223> OTHER INFORMATION: Synthetic sequence: Humanized CDRL 3

<400> SEQUENCE: 9

Gln Gln Arg Ser Thr Ile Pro Pro Thr
1               5

<210> SEQ ID NO 10
<211> LENGTH: 10
<212> TYPE: PRT
<213> ORGANISM: Artificial sequence
<220> FEATURE:
<223> OTHER INFORMATION: Synthetic sequence: Humanized CDRH 1

<400> SEQUENCE: 10

Gly Asp Asp Ile Thr Ser Gly Tyr Trp Asn
1               5                   10
```

-continued

```
<210> SEQ ID NO 11
<211> LENGTH: 10
<212> TYPE: PRT
<213> ORGANISM: Artificial sequence
<220> FEATURE:
<223> OTHER INFORMATION: Synthetic sequence: Humanized CDRH 1

<400> SEQUENCE: 11

Gly Asp Asp Ile Thr Ser Gly Tyr Trp Asp
1               5                   10

<210> SEQ ID NO 12
<211> LENGTH: 10
<212> TYPE: PRT
<213> ORGANISM: Artificial sequence
<220> FEATURE:
<223> OTHER INFORMATION: Synthetic sequence: Humanized CDRH 1

<400> SEQUENCE: 12

Gly Asp Asp Ile Thr Ser Gly Tyr His Asp
1               5                   10

<210> SEQ ID NO 13
<211> LENGTH: 10
<212> TYPE: PRT
<213> ORGANISM: Artificial sequence
<220> FEATURE:
<223> OTHER INFORMATION: Synthetic sequence: Humanized CDRH 1

<400> SEQUENCE: 13

Gly Asp Asp Ile Thr Ser Gly Tyr His Glu
1               5                   10

<210> SEQ ID NO 14
<211> LENGTH: 16
<212> TYPE: PRT
<213> ORGANISM: Artificial sequence
<220> FEATURE:
<223> OTHER INFORMATION: Synthetic sequence: Humanized CDRH 2

<400> SEQUENCE: 14

Tyr Ile Ser Tyr Ser Gly Ser Thr Tyr Tyr Asn Pro Ser Leu Lys Ser
1               5                   10                  15

<210> SEQ ID NO 15
<211> LENGTH: 16
<212> TYPE: PRT
<213> ORGANISM: Artificial sequence
<220> FEATURE:
<223> OTHER INFORMATION: Synthetic sequence: Humanized CDRH 2

<400> SEQUENCE: 15

Tyr Ile Ser Tyr Ser Gly Ser Thr Tyr Tyr Ser Pro Ser Leu Lys Ser
1               5                   10                  15

<210> SEQ ID NO 16
<211> LENGTH: 16
<212> TYPE: PRT
<213> ORGANISM: Artificial sequence
<220> FEATURE:
<223> OTHER INFORMATION: Synthetic sequence: Humanized CDRH 2

<400> SEQUENCE: 16

Tyr Ile Ser Tyr Ser Gly Ser Thr Tyr Tyr Ile Pro Ser Leu Lys Ser
1               5                   10                  15

<210> SEQ ID NO 17
<211> LENGTH: 16
```

```
<212> TYPE: PRT
<213> ORGANISM: Artificial sequence
<220> FEATURE:
<223> OTHER INFORMATION: Synthetic sequence: Humanized CDRH 2

<400> SEQUENCE: 17

Tyr Ile Ser Tyr Ser Gly Ser Thr Gln Tyr Ser Pro Ser Leu Lys Ser
1               5                   10                  15

<210> SEQ ID NO 18
<211> LENGTH: 16
<212> TYPE: PRT
<213> ORGANISM: Artificial sequence
<220> FEATURE:
<223> OTHER INFORMATION: Synthetic sequence: Humanized CDRH 2

<400> SEQUENCE: 18

Tyr Ile Ser Tyr Ser Gly Ser Thr Ser Tyr Ser Pro Ser Leu Lys Ser
1               5                   10                  15

<210> SEQ ID NO 19
<211> LENGTH: 16
<212> TYPE: PRT
<213> ORGANISM: Artificial sequence
<220> FEATURE:
<223> OTHER INFORMATION: Synthetic sequence: Humanized CDRH 2

<400> SEQUENCE: 19

Tyr Ile Ser Tyr Ser Gly Ser Thr Val Tyr Ser Pro Ser Leu Lys Ser
1               5                   10                  15

<210> SEQ ID NO 20
<211> LENGTH: 14
<212> TYPE: PRT
<213> ORGANISM: Artificial sequence
<220> FEATURE:
<223> OTHER INFORMATION: Synthetic sequence: Humanized CDRH 3

<400> SEQUENCE: 20

Pro Pro Gly Tyr Tyr Gly Phe Gly Pro Tyr Ala Met Asp Tyr
1               5                   10

<210> SEQ ID NO 21
<211> LENGTH: 14
<212> TYPE: PRT
<213> ORGANISM: Artificial sequence
<220> FEATURE:
<223> OTHER INFORMATION: Synthetic sequence: Humanized CDRH 3

<400> SEQUENCE: 21

Pro Pro Gly Tyr Tyr Gly Phe Gly Pro Tyr Ala Leu Asp Tyr
1               5                   10

<210> SEQ ID NO 22
<211> LENGTH: 14
<212> TYPE: PRT
<213> ORGANISM: Artificial sequence
<220> FEATURE:
<223> OTHER INFORMATION: Synthetic sequence: Humanized CDRH 3

<400> SEQUENCE: 22

Pro Pro Ala Tyr Tyr Gly Phe Gly Pro Tyr Ala Leu Asp Tyr
1               5                   10

<210> SEQ ID NO 23
<211> LENGTH: 23
<212> TYPE: PRT
<213> ORGANISM: Homo sapiens
```

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 24
<211> LENGTH: 15
<212> TYPE: PRT
<213> ORGANISM: Homo sapiens

<400> SEQUENCE: 24

Trp Tyr Gln Gln Lys Pro Gly Lys Ala Pro Lys Leu Leu Ile Tyr
1               5                   10                  15

<210> SEQ ID NO 25
<211> LENGTH: 32
<212> TYPE: PRT
<213> ORGANISM: Homo sapiens

<400> SEQUENCE: 25

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 26
<211> LENGTH: 10
<212> TYPE: PRT
<213> ORGANISM: Homo sapiens

<400> SEQUENCE: 26

Phe Gly Gly Gly Thr Lys Val Glu Ile Lys
1               5                   10

<210> SEQ ID NO 27
<211> LENGTH: 25
<212> TYPE: PRT
<213> ORGANISM: Homo sapiens

<400> SEQUENCE: 27

Gln Val Gln Leu Gln Glu Ser Gly Pro Gly Leu Val Lys Pro Ser Glu
1               5                   10                  15

Thr Leu Ser Leu Thr Cys Thr Val Ser
            20                  25

<210> SEQ ID NO 28
<211> LENGTH: 14
<212> TYPE: PRT
<213> ORGANISM: Homo sapiens

<400> SEQUENCE: 28

Trp Ile Arg Gln Pro Pro Gly Lys Gly Leu Glu Trp Ile Gly
1               5                   10

<210> SEQ ID NO 29
<211> LENGTH: 32
<212> TYPE: PRT
<213> ORGANISM: Homo sapiens

<400> SEQUENCE: 29

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 30
<211> LENGTH: 11
<212> TYPE: PRT
<213> ORGANISM: Homo sapiens

<400> SEQUENCE: 30

Trp Gly Gln Gly Thr Leu Val Thr Val Ser Ser
1               5                   10

<210> SEQ ID NO 31
<211> LENGTH: 451
<212> TYPE: PRT
<213> ORGANISM: Homo sapiens

<400> SEQUENCE: 31

Gln Val Met Asp Phe Leu Phe Glu Lys Trp Lys Leu Tyr Gly Asp Gln
1               5                   10                  15

Cys His His Asn Leu Ser Leu Leu Pro Pro Thr Glu Leu Val Cys
            20                  25                  30

Asn Arg Thr Phe Asp Lys Tyr Ser Cys Trp Pro Asp Thr Pro Ala Asn
            35                  40                  45

Thr Thr Ala Asn Ile Ser Cys Pro Trp Tyr Leu Pro Trp His His Lys
        50                  55                  60

Val Gln His Arg Phe Val Phe Lys Arg Cys Gly Pro Asp Gly Gln Trp
65                  70                  75                  80

Val Arg Gly Pro Arg Gly Gln Pro Trp Arg Asp Ala Ser Gln Cys Gln
                85                  90                  95

Met Asp Gly Glu Glu Ile Glu Val Gln Lys Glu Val Ala Lys Met Tyr
            100                 105                 110

Ser Ser Phe Gln Val Met Tyr Thr Val Gly Tyr Ser Leu Ser Leu Gly
        115                 120                 125

Ala Leu Leu Leu Ala Leu Ala Ile Leu Gly Gly Leu Ser Lys Leu His
    130                 135                 140

Cys Thr Arg Asn Ala Ile His Ala Asn Leu Phe Ala Ser Phe Val Leu
145                 150                 155                 160

Lys Ala Ser Ser Val Leu Val Ile Asp Gly Leu Leu Arg Thr Arg Tyr
                165                 170                 175

Ser Gln Lys Ile Gly Asp Asp Leu Ser Val Ser Thr Trp Leu Ser Asp
            180                 185                 190

Gly Ala Val Ala Gly Cys Arg Val Ala Ala Val Phe Met Gln Tyr Gly
        195                 200                 205

Ile Val Ala Asn Tyr Cys Trp Leu Leu Val Glu Gly Leu Tyr Leu His
    210                 215                 220

Asn Leu Leu Gly Leu Ala Thr Leu Pro Glu Arg Ser Phe Phe Ser Leu
225                 230                 235                 240

Tyr Leu Gly Ile Gly Trp Gly Ala Pro Met Leu Phe Val Val Pro Trp
                245                 250                 255

Ala Val Val Lys Cys Leu Phe Glu Asn Val Gln Cys Trp Thr Ser Asn
            260                 265                 270

Asp Asn Met Gly Phe Trp Trp Ile Leu Arg Phe Pro Val Phe Leu Ala
        275                 280                 285

Ile Leu Ile Asn Phe Phe Ile Phe Val Arg Ile Val Gln Leu Leu Val
    290                 295                 300

```
Ala Lys Leu Arg Ala Arg Gln Met His His Thr Asp Tyr Lys Phe Arg
305                 310                 315                 320

Leu Ala Lys Ser Thr Leu Thr Leu Ile Pro Leu Leu Gly Val His Glu
            325                 330                 335

Val Val Phe Ala Phe Val Thr Asp Glu His Ala Gln Gly Thr Leu Arg
        340                 345                 350

Ser Ala Lys Leu Phe Phe Asp Leu Phe Leu Ser Ser Phe Gln Gly Leu
        355                 360                 365

Leu Val Ala Val Leu Tyr Cys Phe Leu Asn Lys Glu Val Gln Ser Glu
    370                 375                 380

Leu Arg Arg Arg Trp His Arg Trp Arg Leu Gly Lys Val Leu Trp Glu
385                 390                 395                 400

Glu Arg Asn Thr Ser Asn His Arg Ala Ser Ser Ser Pro Gly His Gly
                405                 410                 415

Pro Pro Ser Lys Glu Leu Gln Phe Gly Arg Gly Gly Ser Gln Asp
            420                 425                 430

Ser Ser Ala Glu Thr Pro Leu Ala Gly Gly Leu Pro Arg Leu Ala Glu
            435                 440                 445

Ser Pro Phe
    450

<210> SEQ ID NO 32
<211> LENGTH: 2034
<212> TYPE: DNA
<213> ORGANISM: Homo sapiens

<400> SEQUENCE: 32
ggatctggca gcgccgcgaa gacgagcggt caccggcgcc cgacccgagc gcgcccagag      60
gacggcgggg agccaagccg accccgagc  agcgccgcgc gggccctgag gctcaaaggg     120
gcagcttcag gggaggacac cccactggcc aggacgcccc aggctctgct gctctgccac    180
tcagctgccc tcggaggagc gtacacacac accaggactg cattgcccca gtgtgcagcc    240
cctgccagat gtgggaggca gctagctgcc cagaggcatg ccccctgcc  agccacagcg    300 accctgctg  ctgttgctgc tgctgctggc ctgccagcca caggtcccct ccgctcaggt    360
gatggacttc ctgtttgaga gtggaagct  ctacggtgac cagtgtcacc acaacctgag    420
cctgctgccc ctcccacgg  agctggtgtg caacagaacc ttcgacaagt attcctgctg    480
gccggacacc cccgccaata ccacggccaa catctcctgc ccctggtacc tgccttggca    540
ccacaaagtg caacaccgct tcgtgttcaa gagatgcggg cccgacggtc agtgggtgcg    600
tggaccccgg gggcagcctt ggcgtgatgc ctcccagtgc agatggatg  cgaggagat     660 tgaggtccag aaggaggtgg ccaagatgta  cagcagcttc  caggtgatgt acacagtggg    720
ctacagcctg tccctggggg ccctgctcct cgccttggcc atcctggggg gcctcagcaa    780
gctgcactgc acccgcaatg ccatccacgc gaatctgttt gcgtccttcg tgctgaaagc    840
cagctccgtg ctggtcattg atgggctgct caggacccgc tacagccaga aaattggcga    900
cgacctcagt gtcagcacct ggctcagtga tggagcggtg gctggctgcc gtgtggccgc    960
ggtgttcatg caatatggca tcgtggccaa ctactgctgg ctgctggtgg agggcctgta   1020
cctgcacaac ctgctgggcc tggccaccct cccgagagg agcttcttca gcctctacct    1080
gggcatcggc tggggtgccc ccatgctgtt cgtcgtcccc tgggcagtgg tcaagtgtct   1140
gttcgagaac gtccagtgct ggaccagcaa tgacaacatg ggcttctggt ggatcctgcg   1200
gttcccggtc ttcctggcca tcctgatcaa cttcttcatc ttcgtccgca tcgttcagct   1260
```

```
gctcgtggcc aagctgcggg cacggcagat gcaccacaca gactacaagt tccggctggc   1320
caagtccacg ctgaccctca tccctctgct gggcgtccac gaagtggtct ttgccttcgt   1380
gacggacgag cacgcccagg gcaccctgcg ctccgccaag ctcttcttcg acctcttcct   1440
cagctccttc cagggcctgc tggtggctgt cctctactgc ttcctcaaca aggaggtgca   1500
gtcggagctg cggcggcgtt ggcaccgctg gcgcctgggc aaagtgctat gggaggagcg   1560
gaacaccagc aaccacaggg cctcatcttc gccccggccac ggccctccca gcaaggagct   1620
```

```
gcagtttggg aggggtggtg gcagccagga ttcatctgcg gagaccccct ggctggtgg    1680 cctccctaga ttggctgaga gccccttctg aaccctgctg gaccccagc tagggctgga    1740 ctctggcacc cagaggcgtc gctggacaac ccagaactgg acgcccagct gaggctgggg   1800 gcggggagc caacagcagc ccccacctac ccccacccc cagtgtggct gtctgcgaga     1860
ttgggcctcc tctccctgca cctgccttgt ccctggtgca gaggtgagca gaggagtcca   1920
gggcgggagt gggggctgtg ccgtgaactg cgtgccagtg tccccacgta tgtcggcacg   1980
tcccatgtgc atggaaatgt cctccaacaa taaagagctc aagtggtcac cgtg         2034
```

<210> SEQ ID NO 33
<211> LENGTH: 458
<212> TYPE: PRT
<213> ORGANISM: Rattus sp.

<400> SEQUENCE: 33

```
Gln Val Met Asp Phe Leu Phe Glu Lys Trp Lys Leu Tyr Ser Asp Gln
1               5                   10                  15

Cys His His Asn Leu Ser Leu Leu Pro Pro Thr Glu Leu Val Cys
            20                  25                  30

Asn Arg Thr Phe Asp Lys Tyr Ser Cys Trp Pro Asp Thr Pro Pro Asn
        35                  40                  45

Thr Thr Ala Asn Ile Ser Cys Pro Trp Tyr Leu Pro Trp Tyr His Lys
    50                  55                  60

Val Gln His Arg Leu Val Phe Lys Arg Cys Gly Pro Asp Gly Gln Trp
65                  70                  75                  80

Val Arg Gly Pro Arg Gly Gln Ser Trp Arg Asp Ala Ser Gln Cys Gln
                85                  90                  95

Met Asp Asp Asp Glu Ile Glu Val Gln Lys Gly Val Ala Lys Met Tyr
            100                 105                 110

Ser Ser Tyr Gln Val Met Tyr Thr Val Gly Tyr Ser Leu Ser Leu Gly
        115                 120                 125

Ala Leu Leu Leu Ala Leu Val Ile Leu Leu Gly Leu Arg Lys Leu His
    130                 135                 140

Cys Thr Arg Asn Tyr Ile His Gly Asn Leu Phe Ala Ser Phe Val Leu
145                 150                 155                 160

Lys Ala Gly Ser Val Leu Val Ile Asp Trp Leu Leu Lys Thr Arg Tyr
                165                 170                 175

Ser Gln Lys Ile Gly Asp Asp Leu Ser Val Ser Val Trp Leu Ser Asp
            180                 185                 190

Gly Ala Val Ala Gly Cys Arg Val Ala Thr Val Ile Met Gln Tyr Gly
        195                 200                 205

Ile Ile Ala Asn Tyr Cys Trp Leu Leu Val Glu Gly Val Tyr Leu Tyr
    210                 215                 220

Ser Leu Leu Ser Ile Thr Thr Phe Ser Glu Lys Ser Phe Phe Ser Leu
225                 230                 235                 240

Tyr Leu Cys Ile Gly Trp Gly Ser Pro Leu Leu Phe Val Ile Pro Trp
```

```
                    245                 250                 255
Val Val Val Lys Cys Leu Phe Glu Asn Val Gln Cys Trp Thr Ser Asn
            260                 265                 270

Asp Asn Met Gly Phe Trp Trp Ile Leu Arg Ile Pro Val Leu Leu Ala
        275                 280                 285

Ile Leu Ile Asn Phe Phe Ile Phe Val Arg Ile Ile His Leu Leu Val
    290                 295                 300

Ala Lys Leu Arg Ala His Gln Met His Tyr Ala Asp Tyr Lys Phe Arg
305                 310                 315                 320

Leu Ala Arg Ser Thr Leu Thr Leu Ile Pro Leu Leu Gly Val His Glu
            325                 330                 335

Val Val Phe Ala Phe Val Thr Asp Glu His Ala Gln Gly Thr Leu Arg
        340                 345                 350

Ser Thr Lys Leu Phe Phe Asp Leu Phe Phe Ser Ser Phe Gln Gly Leu
    355                 360                 365

Leu Val Ala Val Leu Tyr Cys Phe Leu Asn Lys Glu Val Gln Ala Glu
370                 375                 380

Leu Leu Arg Arg Trp Arg Arg Trp Gln Glu Gly Lys Ala Leu Gln Glu
385                 390                 395                 400

Glu Arg Met Ala Ser Ser His Gly Ser His Met Ala Pro Ala Gly Thr
            405                 410                 415

Cys His Gly Asp Pro Cys Glu Lys Leu Gln Leu Met Ser Ala Gly Ser
        420                 425                 430

Ser Ser Gly Thr Gly Cys Glu Pro Ser Ala Lys Thr Ser Leu Ala Ser
    435                 440                 445

Ser Leu Pro Arg Leu Ala Asp Ser Pro Thr
450                 455

<210> SEQ ID NO 34
<211> LENGTH: 1875
<212> TYPE: DNA
<213> ORGANISM: Rattus sp.

<400> SEQUENCE: 34
gaattcgcgg ccgccgccgg gccccagatc ccagtgcgcg aggagcccag tcctagaccc     60
agcaacctga ggagaggtgc acacaccccc aaggacccag gcacccaacc tctgccagat    120
gtgggggggt ggctacccag aggcatgctc ctcacccagc tccactgtcc ctacctgctg    180
ctgctgctgg tggtgctgtc atgtctgcca aaggcaccct gcccaggt aatggacttt      240 ttgtttgaga agtggaagct ctatagtgac cagtgccacc acaacctaag cctgctgccc    300
ccacctactg agctggtctg caacagaact ttcgacaagt actcctgctg gcctgacacc    360
cctcccaaca ccactgccaa catttcctgc ccctggtacc taccttggta ccacaaagtg    420
cagcaccgcc tagtgttcaa gaggtgtggg cctgatgggc agtgggttcg agggccacgg    480
gggcagtcat ggcgcgacgc ctcccaatgt cagatggatg atgacgagat cgaggtccag    540
aagggggtag ccaagatgta tagcagctac caggtgatgt acactgtggg ctacagtctg    600
tccctggggg ccttgctcct ggcgctggtc atcctgctgg cctcaggaa gctgcactgc    660 acccggaact acatccacgg gaacctgttc gcgtccttcg tgctcaaggc tggctctgtg    720
ctggtcattg attggctgct caagacacgc tatagccaga gattggaga tgacctcagt    780 gtgagcgtct ggctcagtga tgggcggtg gctggctgca gagtggccac agtgatcatg    840
cagtacggca tcatagccaa ctactgctgg ttgctggtgg agggtgtgta cctgtacagc    900
ctgctgagca tcaccacctt ctcggagaag agcttcttct ccctctatct gtgcatcggc    960
```

```
tggggatctc ccctgctgtt tgtcatcccc tgggtggtgg tcaagtgtct gtttgagaat    1020
gtccagtgct ggaccagcaa tgacaatatg ggattctggt ggatcctgcg tatccctgta    1080
ctcctggcca tactgatcaa ttttttcatc tttgtccgca tcattcatct tcttgtggcc    1140
aagctgcgtg cccatcagat gcactatgct gattacaagt tccggctagc caggtccacg    1200
ctgaccctca ttcctctgct gggagtccac gaagtggtct ttgcctttgt gactgatgag    1260
catgcccagg gcaccctgcg ctccaccaag ctcttttttg acctgttctt cagctccttt    1320
cagggtctgc tggtggctgt tctctactgt ttcctcaaca aggaggtgca ggcagagcta    1380
ctgcggcgtt ggaggcgatg gcaagaaggc aaagctcttc aggaggaaag gatggccagc    1440
agccatggca gccacatggc cccagcaggg acttgtcatg gtgatccctg tgagaaactt    1500
cagcttatga gtgcaggcag cagcagtggg actggctgtg agccctctgc gaagacctca    1560
ttggccagta gtctcccaag gctggctgac agccccacct gaatctccac tggactccag    1620
ccaagttgga ttcagaaagg gcctcacaag acaacccaga acagatgcc tggccaaggc    1680 tgaagaggca agcagcaag acagcagctt gtactatcca cactccccta acctgtcctg    1740
gccgggtaca ggccacattg atggagtagg ggctggatat gatggagtag ccatgctatg    1800
aactatgggt gttcccatga gtgttgccat gttccatgca cacagatatg accttcagta    1860
aagagctccc gtagg                                                    1875
```

<210> SEQ ID NO 35
<211> LENGTH: 458
<212> TYPE: PRT
<213> ORGANISM: Mus sp.

<400> SEQUENCE: 35

Gln Val Met Asp Phe Leu Phe Glu Lys Trp Lys Leu Tyr Ser Asp Gln
1               5                   10                  15

Cys His His Asn Leu Ser Leu Leu Pro Pro Thr Glu Leu Val Cys
            20                  25                  30

Asn Arg Thr Phe Asp Asn Tyr Ser Cys Trp Pro Asp Thr Pro Pro Asn
        35                  40                  45

Thr Thr Ala Asn Ile Ser Cys Pro Trp Tyr Leu Pro Trp Cys His Lys
    50                  55                  60

Val Gln His Arg Leu Val Phe Lys Arg Cys Gly Pro Asp Gly Gln Trp
65                  70                  75                  80

Val Arg Gly Pro Arg Gly Gln Pro Trp Arg Asn Ala Ser Gln Cys Gln
                85                  90                  95

Leu Asp Asp Glu Glu Ile Glu Val Gln Lys Gly Val Ala Lys Met Tyr
            100                 105                 110

Ser Ser Gln Gln Val Met Tyr Thr Val Gly Tyr Ser Leu Ser Leu Gly
        115                 120                 125

Ala Leu Leu Leu Ala Leu Val Ile Leu Leu Gly Leu Arg Lys Leu His
    130                 135                 140

Cys Thr Arg Asn Tyr Ile His Gly Asn Leu Phe Ala Ser Phe Val Leu
145                 150                 155                 160

Lys Ala Gly Ser Val Leu Val Ile Asp Trp Leu Leu Lys Thr Arg Tyr
                165                 170                 175

Ser Gln Lys Ile Gly Asp Asp Leu Ser Val Ser Val Trp Leu Ser Asp
            180                 185                 190

Gly Ala Met Ala Gly Cys Arg Val Ala Thr Val Ile Met Gln Tyr Gly
        195                 200                 205

| Ile | Ile | Pro | Asn | Tyr | Cys | Trp | Leu | Leu | Val | Glu | Gly | Val | Tyr | Leu | Tyr |
| 210 | | | | 215 | | | | | 220 | | | | | | |

Ser Leu Leu Ser Leu Ala Thr Phe Ser Glu Arg Ser Phe Phe Ser Leu
225                 230                 235                 240

Tyr Leu Gly Ile Gly Trp Gly Ala Pro Leu Leu Phe Val Ile Pro Trp
                245                 250                 255

Val Val Val Lys Cys Leu Phe Glu Asn Val Gln Cys Trp Thr Ser Asn
            260                 265                 270

Asp Asn Met Gly Phe Trp Trp Ile Leu Arg Ile Pro Val Phe Leu Ala
        275                 280                 285

Leu Leu Ile Asn Phe Phe Ile Phe Val His Ile Ile Gln Leu Leu Val
290                 295                 300

Ala Lys Leu Arg Ala His Gln Met His Tyr Ala Asp Tyr Lys Phe Arg
305                 310                 315                 320

Leu Ala Arg Ser Thr Leu Thr Leu Ile Pro Leu Leu Gly Val His Glu
                325                 330                 335

Val Val Phe Ala Phe Val Thr Asp Glu His Ala Gln Gly Thr Leu Arg
            340                 345                 350

Ser Thr Lys Leu Phe Phe Asp Leu Phe Leu Ser Ser Phe Gln Gly Leu
        355                 360                 365

Leu Val Ala Val Leu Tyr Cys Phe Leu Asn Lys Glu Val Gln Ala Glu
370                 375                 380

Leu Met Arg Arg Trp Arg Gln Trp Gln Glu Gly Lys Ala Leu Gln Glu
385                 390                 395                 400

Glu Arg Leu Ala Ser Ser His Gly Ser His Met Ala Pro Ala Gly Pro
                405                 410                 415

Cys His Gly Asp Pro Cys Glu Lys Leu Gln Leu Met Ser Ala Gly Ser
            420                 425                 430

Ser Ser Gly Thr Gly Cys Val Pro Ser Met Glu Thr Ser Leu Ala Ser
        435                 440                 445

Ser Leu Pro Arg Leu Ala Asp Ser Pro Thr
    450                 455

<210> SEQ ID NO 36
<211> LENGTH: 1944
<212> TYPE: DNA
<213> ORGANISM: Mus sp.

<400> SEQUENCE: 36

```
cagggtctcc cttgcaacct gaggagaggt gcacacactc tgaggaccta ggtgtgcaac      60
ctctgccaga tgtggggcgt ggctacccag aggcatgccc ctcacccagc tccactgtcc     120
ccacctgctg ctgctgctgt tggtgctgtc atgtctgcca gaggcaccct ctgcccaggt     180
aatggacttt ttgtttgaga agtggaagct ctatagtgac caatgtcacc acaacctaag     240
cctgctgccc ccacctactg agctggtctg taacagaacc ttcgacaact actcctgctg     300
gcctgacacc cctcccaaca ccactgccaa catttcctgc ccctggtacc taccttggtg     360
ccacaaagtg cagcaccgcc tagtgttcaa gaggtgtggg cccgatgggc agtgggttcg     420
agggccacgg gggcagccgt ggcgcaacgc ctcccaatgt cagttggatg atgaagagat     480
cgaggtccag aagggggtgg ccaagatgta tagcagccag caggtgatgt acaccgtggg     540
ctacagtctg tccctggggg ccttgctcct tgcgctggtc atcctgctgg gcctcaggaa     600
gctgcactgc acccgaaact acatccatgg gaacctgttt gcgtcctttg tgctcaaggc     660
tggctctgtg ttggtcatcg attggctgct gaagacacgg tacagccaga agattggcga     720
```

```
tgacctcagt gtgagcgtct ggctcagtga cggggcgatg gccggctgca gagtggccac    780
agtgatcatg cagtacggca tcatacccaa ctattgctgg ttgctggtag agggcgtgta    840
cctgtacagc ctgctgagcc ttgccacctt ctctgagagg agcttctttt ccctctacct    900
gggcattggc tggggtgcgc ccctgctgtt tgtcatcccc tgggtggtgg tcaagtgtct    960
gtttgagaat gttcagtgct ggaccagcaa tgacaacatg ggattctggt ggatcctgcg   1020
tattcctgtc ttcctggcct tactgatcaa tttttttcatc tttgtccaca tcattcaact   1080
tcttgtggcc aagctgcgtg cccatcagat gcactatgct gattacaagt tccggctggc   1140
caggtccacg ctgacgctca tccctctgct gggggtccac gaggtggtct ttgcctttgt   1200
gactgacgag catgcccaag gcaccctgcg ctccaccaag ctcttttttg acctgttcct   1260
cagctccttc cagggtctgc tggtggctgt tctctactgt ttcctcaaca aggaggtgca   1320
ggcagagctg atgcggcgtt ggaggcaatg gcaagaaggc aaagctcttc aggaggaaag   1380
gttggccagc agccatggca gccacatggc cccagcaggg ccttgtcatg gtgatccctg   1440
tgagaaactt cagcttatga gtgcaggcag cagcagtggg actggctgtg tgccctctat   1500
ggagacctcg ctggccagta gtctcccaag gttggctgac agcccacct gaatctccac    1560
ttggagccta ggcaggttgt gttcaagaaa gggcctcaga ggacaaccca gagccagatg   1620
cccggccaag gttgaagagc caaagcagca agacagcagc ttgtactgtg cacactcccc   1680
taacctgtcc tagcctggca caggccacag tgacagagta ggggttggat atgatggaga   1740
agccatgtta tctatgaact ctgagtgttc ccatgtgtgt tgacatggtc cctgtaccca   1800
gatatgtcct tcagtaaaaa gctcgagtgg agctgctgca cagctcgtgg acagcaggct   1860
tgaagccccc agggacgggg tttgggaggc cggggatgag cagcacactc agcaggtgga   1920
gcgctagtgc aacccaggaa agaa                                          1944
```

<210> SEQ ID NO 37
<211> LENGTH: 451
<212> TYPE: PRT
<213> ORGANISM: Macaca fascicularis

<400> SEQUENCE: 37

```
Gln Val Met Asp Phe Leu Phe Glu Lys Trp Lys Leu Tyr Gly Asp Gln
1               5                   10                  15

Cys His His Asn Leu Ser Leu Leu Pro Pro Thr Glu Leu Val Cys
            20                  25                  30

Asn Arg Thr Phe Asp Lys Tyr Ser Cys Trp Pro Asp Thr Pro Ala Asn
        35                  40                  45

Thr Thr Ala Asn Ile Ser Cys Pro Trp Tyr Leu Pro Trp His His Lys
    50                  55                  60

Val Gln His Arg Phe Val Phe Lys Arg Cys Gly Pro Asp Gly Gln Trp
65                  70                  75                  80

Val Arg Gly Pro Arg Gly Gln Pro Trp Arg Asp Ala Ser Gln Cys Gln
                85                  90                  95

Met Asp Gly Glu Glu Leu Glu Val Gln Lys Glu Val Ala Lys Met Tyr
            100                 105                 110

Ser Ser Phe Gln Val Met Tyr Thr Val Gly Tyr Ser Leu Ser Leu Gly
        115                 120                 125

Ala Leu Leu Leu Ala Leu Ala Val Leu Gly Gly Ile Ser Lys Leu His
    130                 135                 140

Cys Thr Arg Asn Ala Ile His Ala Asn Leu Phe Val Ser Phe Val Leu
145                 150                 155                 160
```

```
Lys Ala Ser Ser Val Leu Val Ile Asp Gly Leu Leu Arg Thr Arg Tyr
                165                 170                 175

Ser Gln Lys Ile Gly Asp Asp Leu Ser Val Ser Ile Trp Leu Ser Asp
            180                 185                 190

Gly Ala Val Ala Gly Cys Arg Val Ala Ala Val Phe Met Gln Tyr Gly
        195                 200                 205

Val Val Ala Asn Tyr Cys Trp Leu Leu Val Glu Gly Leu Tyr Leu His
    210                 215                 220

Asn Leu Leu Gly Leu Ala Thr Leu Pro Glu Arg Ser Phe Phe Ser Leu
225                 230                 235                 240

Tyr Leu Gly Ile Gly Trp Gly Ala Pro Met Leu Phe Ile Ile Pro Trp
                245                 250                 255

Val Val Val Arg Cys Leu Phe Glu Asn Ile Gln Cys Trp Thr Ser Asn
            260                 265                 270

Asp Asn Met Gly Phe Trp Trp Ile Leu Arg Phe Pro Val Phe Leu Ala
        275                 280                 285

Ile Leu Ile Asn Phe Phe Ile Phe Ile Arg Ile Val His Leu Leu Val
    290                 295                 300

Ala Lys Leu Arg Ala Arg Glu Met His His Thr Asp Tyr Lys Phe Arg
305                 310                 315                 320

Leu Ala Lys Ser Thr Leu Thr Leu Ile Pro Leu Leu Gly Val His Glu
                325                 330                 335

Val Val Phe Ala Phe Val Thr Asp Glu His Ala Gln Gly Thr Leu Arg
            340                 345                 350

Phe Ala Lys Leu Phe Phe Asp Leu Phe Leu Ser Ser Phe Gln Gly Leu
        355                 360                 365

Leu Val Ala Val Leu Tyr Cys Phe Leu Asn Lys Glu Val Gln Ser Glu
370                 375                 380

Leu Arg Arg His Trp His Arg Trp Arg Leu Gly Lys Val Leu Gln Glu
                385                 390                 395                 400

Glu Arg Gly Thr Ser Asn His Lys Ala Pro Ser Ala Pro Gly Gln Gly
                405                 410                 415

Leu Pro Gly Lys Lys Leu Gln Ser Gly Arg Asp Gly Ser Gln Asp
        420                 425                 430

Ser Ser Ala Glu Ile Pro Leu Ala Gly Gly Leu Pro Arg Leu Ala Glu
            435                 440                 445

Ser Pro Phe
    450

<210> SEQ ID NO 38
<211> LENGTH: 1434
<212> TYPE: DNA
<213> ORGANISM: Macaca fascicularis

<400> SEQUENCE: 38
atgccgccgt gccagccgcg ccgcccgctg ctgctgctgc tgctgctgct ggcgtgccag      60
ccgcaggcgc cgagcgcgca ggtgatggat tttctgtttg aaaaatggaa actgtatggc     120
gatcagtgcc atcataacct gagcctgctg ccgccgccga ccgaactggt gtgcaaccgc     180
acctttgata aatatagctg ctggccggat accccggcga caccaccgc gaacattagc      240 tgcccgtggt atctgccgtg gcatcataaa gtgcagcatc gctttgtgtt taaacgctgc     300
ggcccggatg gccagtgggt gcgcggcccg cgcggccagc cgtggcgcga tgcgagccag     360
tgccagatgg atggcgaaga actggaagtg cagaaagaag tggcgaaaat gtatagcagc     420
tttcaggtga tgtataccgt gggctatagc ctgagcctgg cgcgctgct gctggcgctg      480
```

```
gcggtgctgg gcggcattag caaactgcat tgcacccgca acgcgattca tgcgaacctg    540
tttgtgagct ttgtgctgaa agcgagcagc gtgctggtga ttgatggcct gctgcgcacc    600
cgctatagcc agaaaattgg cgatgatctg agcgtgagca tttggctgag cgatggcgcg    660
gtggcgggct gccgcgtggc ggcggtgttt atgcagtatg gcgtggtggc gaactattgc    720
tggctgctgg tggaaggcct gtatctgcat aacctgctgg gcctggcgac cctgccggaa    780
cgcagctttt ttagcctgta tctgggcatt ggctggggcg cgccgatgct gtttattatt    840
ccgtgggtgg tggtgcgctg cctgtttgaa acattcagt gctggaccag caacgataac    900
atgggctttt ggtggattct cgctttccg gtgtttctgg cgattctgat taactttttt    960
atttttattc gcattgtgca tctgctggtg gcgaaactgc gcgcgcgcga aatgcatcat    1020
accgattata aatttcgcct ggcgaaaagc accctgaccc tgattccgct gctgggcgtg    1080
catgaagtgg tgtttgcgtt tgtgaccgat gaacatgcgc agggcaccct gcgctttgcg    1140
aaactgtttt ttgatctgtt tctgagcagc tttcagggcc tgctggtggc ggtgctgtat    1200
tgctttctga caaagaagt gcagagcgaa ctgcgccgcc attggcatcg ctggcgcctg    1260
ggcaaagtgc tgcaggaaga acgcggcacc agcaaccata agcgccgag cgcgccgggc    1320 cagggcctgc cgggcaaaaa actgcagagc ggccgcgatg gcggcagcca ggatagcagc    1380
gcggaaattc cgctggcggg cggcctgccg cgcctggcgg aaagcccgtt ttaa            1434
```

<210> SEQ ID NO 39
<211> LENGTH: 106
<212> TYPE: PRT
<213> ORGANISM: Artificial sequence
<220> FEATURE:
<223> OTHER INFORMATION: Synthetic sequence: Humanized variable light
      chain

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

His Trp Tyr Gln Gln Lys Pro Gly Lys Ala Pro Lys Leu Leu Ile Tyr
        35                  40                  45

Thr Thr Ser Asn Leu Ala His Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Trp Arg Ser Thr Leu Pro Pro Thr
                85                  90                  95

Phe Gly Gly Gly Thr Lys Val Glu Ile Lys
            100                 105

<210> SEQ ID NO 40
<211> LENGTH: 122
<212> TYPE: PRT
<213> ORGANISM: Artificial sequence
<220> FEATURE:
<223> OTHER INFORMATION: Synthetic sequence: Humanized variable heavy
      chain

<400> SEQUENCE: 40

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Asp Ile Thr Ser Gly

```
                    20                  25                  30
Tyr Trp Asp Trp Ile Arg Gln Pro Pro Gly Lys Gly Leu Glu Trp Ile
            35                  40                  45

Gly Tyr Ile Ser Tyr Ser Gly Ser Thr Tyr Tyr Ser Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Pro Pro Gly Tyr Tyr Gly Phe Gly Pro Tyr Ala Leu Asp Tyr Trp
            100                 105                 110

Gly Gln Gly Thr Leu Val Thr Val Ser Ser
            115                 120

<210> SEQ ID NO 41
<211> LENGTH: 106
<212> TYPE: PRT
<213> ORGANISM: Artificial sequence
<220> FEATURE:
<223> OTHER INFORMATION: Synthetic sequence: Humanized variable light
      chain

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Ser Tyr Ser Ser Ser Val Ser Tyr Met
            20                  25                  30

His Trp Tyr Gln Gln Lys Pro Gly Lys Ala Pro Lys Leu Leu Ile Tyr
        35                  40                  45

Thr Thr Ser Asn Leu Ala His Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Arg Ser Thr Leu Pro Pro Thr
                85                  90                  95

Phe Gly Gly Gly Thr Lys Val Glu Ile Lys
            100                 105

<210> SEQ ID NO 42
<211> LENGTH: 122
<212> TYPE: PRT
<213> ORGANISM: Artificial sequence
<220> FEATURE:
<223> OTHER INFORMATION: Synthetic sequence: Humanized variable heavy
      chain

<400> SEQUENCE: 42

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Asp Ile Thr Ser Gly
            20                  25                  30

Tyr Trp Asn Trp Ile Arg Gln Pro Pro Gly Lys Gly Leu Glu Trp Ile
        35                  40                  45

Gly Tyr Ile Ser Tyr Ser Gly Ser Thr Tyr Tyr Ile Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95
```

```
Arg Pro Pro Gly Tyr Tyr Gly Phe Gly Pro Tyr Ala Met Asp Tyr Trp
            100                 105                 110

Gly Gln Gly Thr Leu Val Thr Val Ser Ser
            115                 120

<210> SEQ ID NO 43
<211> LENGTH: 106
<212> TYPE: PRT
<213> ORGANISM: Artificial sequence
<220> FEATURE:
<223> OTHER INFORMATION: Synthetic sequence: Humanized variable light
      chain

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Ile
            20                  25                  30

His Trp Tyr Gln Gln Lys Pro Gly Lys Ala Pro Lys Leu Leu Ile Tyr
            35                  40                  45

Thr Thr Ser Tyr Leu Ala His Gly Val Pro Ser Arg Phe Ser Gly Ser
50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Leu Gln Arg Ser Thr Leu Pro Pro Thr
                85                  90                  95

Phe Gly Gly Gly Thr Lys Val Glu Ile Lys
            100                 105

<210> SEQ ID NO 44
<211> LENGTH: 122
<212> TYPE: PRT
<213> ORGANISM: Artificial sequence
<220> FEATURE:
<223> OTHER INFORMATION: Synthetic sequence: Humanized variable heavy
      chain

<400> SEQUENCE: 44

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Asp Ile Thr Ser Gly
            20                  25                  30

Tyr Trp Asp Trp Ile Arg Gln Pro Pro Gly Lys Gly Leu Glu Trp Ile
            35                  40                  45

Gly Tyr Ile Ser Tyr Ser Gly Ser Thr Tyr Tyr Ser Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Pro Pro Gly Tyr Tyr Gly Phe Gly Pro Tyr Ala Leu Asp Tyr Trp
            100                 105                 110

Gly Gln Gly Thr Leu Val Thr Val Ser Ser
            115                 120

<210> SEQ ID NO 45
<211> LENGTH: 106
<212> TYPE: PRT
<213> ORGANISM: Artificial sequence
<220> FEATURE:
```

-continued

<223> OTHER INFORMATION: Synthetic sequence: Humanized variable light
     chain

<400> SEQUENCE: 45

Asp Ile Gln Met Thr Gln Ser Pro Ser Leu Ser Ala Ser Val Gly
1               5                   10                  15

Asp Arg Val Thr Ile Thr Cys Ser Ala Ser Ser Ser Val Ser Tyr Ile
            20                  25                  30

His Trp Tyr Gln Gln Lys Pro Gly Lys Ala Pro Lys Leu Leu Ile Tyr
        35                  40                  45

Thr Thr Ser Tyr Leu Ala His Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Arg Ser Thr Leu Pro Pro Thr
                85                  90                  95

Phe Gly Gly Gly Thr Lys Val Glu Ile Lys
            100                 105

<210> SEQ ID NO 46
<211> LENGTH: 122
<212> TYPE: PRT
<213> ORGANISM: Artificial sequence
<220> FEATURE:
<223> OTHER INFORMATION: Synthetic sequence: Humanized variable heavy
     chain

<400> SEQUENCE: 46

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Asp Ile Thr Ser Gly
            20                  25                  30

Tyr His Asp Trp Ile Arg Gln Pro Pro Gly Lys Gly Leu Glu Trp Ile
        35                  40                  45

Gly Tyr Ile Ser Tyr Ser Gly Ser Thr Tyr Tyr Ser Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Pro Pro Gly Tyr Tyr Gly Phe Gly Pro Tyr Ala Leu Asp Tyr Trp
            100                 105                 110

Gly Gln Gly Thr Leu Val Thr Val Ser Ser
        115                 120

<210> SEQ ID NO 47
<211> LENGTH: 122
<212> TYPE: PRT
<213> ORGANISM: Artificial sequence
<220> FEATURE:
<223> OTHER INFORMATION: Synthetic sequence: Humanized variable heavy
     chain

<400> SEQUENCE: 47

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Asp Ile Thr Ser Gly
            20                  25                  30

Tyr His Asp Trp Ile Arg Gln Pro Pro Gly Lys Gly Leu Glu Trp Ile
        35                  40                  45

```
Gly Tyr Ile Ser Tyr Ser Gly Ser Thr Gln Tyr Ser Pro Ser Leu Lys
        50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                85                  90                  95

Arg Pro Pro Gly Tyr Tyr Gly Phe Gly Pro Tyr Ala Leu Asp Tyr Trp
            100                 105                 110

Gly Gln Gly Thr Leu Val Thr Val Ser Ser
            115                 120

<210> SEQ ID NO 48
<211> LENGTH: 122
<212> TYPE: PRT
<213> ORGANISM: Artificial sequence
<220> FEATURE:
<223> OTHER INFORMATION: Synthetic sequence: Humanized variable heavy
      chain

<400> SEQUENCE: 48

Gln Val Gln Leu Gln Glu Ser Gly Pro Gly Leu Val Lys Pro Ser Glu
 1               5                  10                  15

Thr Leu Ser Leu Thr Cys Thr Val Ser Gly Asp Asp Ile Thr Ser Gly
                20                  25                  30

Tyr His Asp Trp Ile Arg Gln Pro Pro Gly Lys Gly Leu Glu Trp Ile
            35                  40                  45

Gly Tyr Ile Ser Tyr Ser Gly Ser Thr Tyr Tyr Ser Pro Ser Leu Lys
        50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                85                  90                  95

Arg Pro Pro Ala Tyr Tyr Gly Phe Gly Pro Tyr Ala Leu Asp Tyr Trp
            100                 105                 110

Gly Gln Gly Thr Leu Val Thr Val Ser Ser
            115                 120

<210> SEQ ID NO 49
<211> LENGTH: 122
<212> TYPE: PRT
<213> ORGANISM: Artificial sequence
<220> FEATURE:
<223> OTHER INFORMATION: Synthetic sequence: Humanized variable heavy
      chain

<400> SEQUENCE: 49

Gln Val Gln Leu Gln Glu Ser Gly Pro Gly Leu Val Lys Pro Ser Glu
 1               5                  10                  15

Thr Leu Ser Leu Thr Cys Thr Val Ser Gly Asp Asp Ile Thr Ser Gly
                20                  25                  30

Tyr His Glu Trp Ile Arg Gln Pro Pro Gly Lys Gly Leu Glu Trp Ile
            35                  40                  45

Gly Tyr Ile Ser Tyr Ser Gly Ser Thr Ser Tyr Ser Pro Ser Leu Lys
        50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                85                  90                  95
```

```
Arg Pro Pro Ala Tyr Tyr Gly Phe Gly Pro Tyr Ala Leu Asp Tyr Trp
            100                 105                 110

Gly Gln Gly Thr Leu Val Thr Val Ser Ser
            115                 120

<210> SEQ ID NO 50
<211> LENGTH: 107
<212> TYPE: PRT
<213> ORGANISM: Homo sapiens

<400> SEQUENCE: 50

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 51
<211> LENGTH: 98
<212> TYPE: PRT
<213> ORGANISM: Homo sapiens

<400> SEQUENCE: 51

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val

<210> SEQ ID NO 52
<211> LENGTH: 229
<212> TYPE: PRT
<213> ORGANISM: Artificial sequence
<220> FEATURE:
<223> OTHER INFORMATION: Synthetic sequence: Modified human IgG4 Fc
      sequence
<220> FEATURE:
<221> NAME/KEY: VARIANT
<222> LOCATION: (10)..(10)
<223> OTHER INFORMATION: Xaa is Ser or Pro
<220> FEATURE:
<221> NAME/KEY: VARIANT
<222> LOCATION: (15)..(15)
<223> OTHER INFORMATION: Xaa is Pro or Glu
<220> FEATURE:
```

```
<221> NAME/KEY: VARIANT
<222> LOCATION: (16)..(16)
<223> OTHER INFORMATION: Xaa is Ala or Val or Phe
<220> FEATURE:
<221> NAME/KEY: VARIANT
<222> LOCATION: (17)..(17)
<223> OTHER INFORMATION: Xaa is Ala or Glu or Leu
<220> FEATURE:
<221> NAME/KEY: VARIANT
<222> LOCATION: (79)..(79)
<223> OTHER INFORMATION: Xaa is Ala or Asn
<220> FEATURE:
<221> NAME/KEY: VARIANT
<222> LOCATION: (229)..(229)
<223> OTHER INFORMATION: Xaa is Lys or deleted

<400> SEQUENCE: 52

Glu Ser Lys Tyr Gly Pro Pro Cys Pro Xaa Cys Pro Ala Pro Xaa Xaa
1               5                   10                  15

Xaa Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Xaa Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Xaa
225

<210> SEQ ID NO 53
<211> LENGTH: 10
<212> TYPE: PRT
<213> ORGANISM: Artificial sequence
<220> FEATURE:
<223> OTHER INFORMATION: Synthetic sequence: Light chain CDR1
<220> FEATURE:
<221> NAME/KEY: VARIANT
<222> LOCATION: (2)..(2)
<223> OTHER INFORMATION: Xaa is Tyr or Ala
<220> FEATURE:
<221> NAME/KEY: VARIANT
<222> LOCATION: (9)..(9)
<223> OTHER INFORMATION: Xaa is Met or Ile

<400> SEQUENCE: 53
```

```
Ser Xaa Ser Ser Ser Val Ser Tyr Xaa His
1               5                   10

<210> SEQ ID NO 54
<211> LENGTH: 7
<212> TYPE: PRT
<213> ORGANISM: Artificial sequence
<220> FEATURE:
<223> OTHER INFORMATION: Synthetic sequence: Light chain CDR2
<220> FEATURE:
<221> NAME/KEY: VARIANT
<222> LOCATION: (4)..(4)
<223> OTHER INFORMATION: Xaa is Asn or Tyr

<400> SEQUENCE: 54

Thr Thr Ser Xaa Leu Ala His
1               5

<210> SEQ ID NO 55
<211> LENGTH: 9
<212> TYPE: PRT
<213> ORGANISM: Artificial sequence
<220> FEATURE:
<223> OTHER INFORMATION: Synthetic sequence: Light chain CDR3
<220> FEATURE:
<221> NAME/KEY: VARIANT
<222> LOCATION: (1)..(1)
<223> OTHER INFORMATION: Xaa is Gln or Leu
<220> FEATURE:
<221> NAME/KEY: VARIANT
<222> LOCATION: (2)..(2)
<223> OTHER INFORMATION: Xaa is Gln or Trp
<220> FEATURE:
<221> NAME/KEY: VARIANT
<222> LOCATION: (6)..(6)
<223> OTHER INFORMATION: Xaa is Leu or Ile

<400> SEQUENCE: 55

Xaa Xaa Arg Ser Thr Xaa Pro Pro Thr
1               5

<210> SEQ ID NO 56
<211> LENGTH: 10
<212> TYPE: PRT
<213> ORGANISM: Artificial sequence
<220> FEATURE:
<223> OTHER INFORMATION: Synthetic sequence: Heavy chain CDR1
<220> FEATURE:
<221> NAME/KEY: VARIANT
<222> LOCATION: (9)..(9)
<223> OTHER INFORMATION: Xaa is Trp or His
<220> FEATURE:
<221> NAME/KEY: VARIANT
<222> LOCATION: (10)..(10)
<223> OTHER INFORMATION: Xaa is Asn, Asp or Glu

<400> SEQUENCE: 56

Gly Asp Asp Ile Thr Ser Gly Tyr Xaa Xaa
1               5                   10

<210> SEQ ID NO 57
<211> LENGTH: 16
<212> TYPE: PRT
<213> ORGANISM: Artificial sequence
<220> FEATURE:
<223> OTHER INFORMATION: Synthetic sequence: Heavy chain CDR2
<220> FEATURE:
<221> NAME/KEY: VARIANT
<222> LOCATION: (9)..(9)
<223> OTHER INFORMATION: Xaa is Tyr, Gln, Ser or Val
<220> FEATURE:
<221> NAME/KEY: VARIANT
```

```
<222> LOCATION: (11)..(11)
<223> OTHER INFORMATION: Xaa is Asn, Ser or Ile

<400> SEQUENCE: 57

Tyr Ile Ser Tyr Ser Gly Ser Thr Xaa Tyr Xaa Pro Ser Leu Lys Ser
1               5                   10                  15

<210> SEQ ID NO 58
<211> LENGTH: 14
<212> TYPE: PRT
<213> ORGANISM: Artificial sequence
<220> FEATURE:
<223> OTHER INFORMATION: Synthetic sequence: Heavy chain CDR3
<220> FEATURE:
<221> NAME/KEY: VARIANT
<222> LOCATION: (3)..(3)
<223> OTHER INFORMATION: Xaa is Gly or Ala
<220> FEATURE:
<221> NAME/KEY: VARIANT
<222> LOCATION: (12)..(12)
<223> OTHER INFORMATION: Xaa is Met or Leu

<400> SEQUENCE: 58

Pro Pro Xaa Tyr Tyr Gly Phe Gly Pro Tyr Ala Xaa Asp Tyr
1               5                   10

<210> SEQ ID NO 59
<211> LENGTH: 213
<212> TYPE: PRT
<213> ORGANISM: Artificial sequence
<220> FEATURE:
<223> OTHER INFORMATION: Synthetic sequence: Humanized monoclonal
      antibody light chain

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
                20                  25                  30

His Trp Tyr Gln Gln Lys Pro Gly Lys Ala Pro Lys Leu Leu Ile Tyr
            35                  40                  45

Thr Thr Ser Asn Leu Ala His Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Trp Arg Ser Thr Leu Pro Pro Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
```

<210> SEQ ID NO 60
<211> LENGTH: 448
<212> TYPE: PRT
<213> ORGANISM: Artificial sequence
<220> FEATURE:
<223> OTHER INFORMATION: Synthetic sequence: Humanized monoclonal antibody heavy chain

<400> SEQUENCE: 60

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Asp Ile Thr Ser Gly
            20                  25                  30

Tyr Trp Asp Trp Ile Arg Gln Pro Pro Gly Lys Gly Leu Glu Trp Ile
        35                  40                  45

Gly Tyr Ile Ser Tyr Ser Gly Ser Thr Tyr Tyr Ser Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Pro Pro Gly Tyr Tyr Gly Phe Gly Pro Tyr Ala Leu Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
```

```
                355                 360                 365
Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

<210> SEQ ID NO 61
<211> LENGTH: 213
<212> TYPE: PRT
<213> ORGANISM: Artificial sequence
<220> FEATURE:
<223> OTHER INFORMATION: Synthetic sequence: Humanized monoclonal
      antibody light chain

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Ser Tyr Ser Ser Val Ser Tyr Met
            20                  25                  30

His Trp Tyr Gln Gln Lys Pro Gly Lys Ala Pro Lys Leu Leu Ile Tyr
        35                  40                  45

Thr Thr Ser Asn Leu Ala His Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Arg Ser Thr Leu Pro Pro Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 62
<211> LENGTH: 448
<212> TYPE: PRT
<213> ORGANISM: Artificial sequence
<220> FEATURE:
<223> OTHER INFORMATION: Synthetic sequence: Humanized monoclonal
      antibody heavy chain

<400> SEQUENCE: 62
```

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Asp Ile Thr Ser Gly
            20                  25                  30

Tyr Trp Asn Trp Ile Arg Gln Pro Pro Gly Lys Gly Leu Glu Trp Ile
        35                  40                  45

Gly Tyr Ile Ser Tyr Ser Gly Ser Thr Tyr Tyr Ile Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Pro Pro Gly Tyr Tyr Gly Phe Gly Pro Tyr Ala Met Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
```

```
                    420             425             430
Ala Leu His Asn His Tyr Thr Gln Lys Ser Leu Ser Leu Ser Leu Gly
            435                 440                 445

<210> SEQ ID NO 63
<211> LENGTH: 213
<212> TYPE: PRT
<213> ORGANISM: Artificial sequence
<220> FEATURE:
<223> OTHER INFORMATION: Synthetic sequence: Humanized monoclonal
      antibody light chain

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Ser Tyr Ile
            20                  25                  30

His Trp Tyr Gln Gln Lys Pro Gly Lys Ala Pro Lys Leu Leu Ile Tyr
            35                  40                  45

Thr Thr Ser Tyr Leu Ala His Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Leu Gln Arg Ser Thr Leu Pro Pro Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 64
<211> LENGTH: 448
<212> TYPE: PRT
<213> ORGANISM: Artificial sequence
<220> FEATURE:
<223> OTHER INFORMATION: Synthetic sequence: Humanized monoclonal
      antibody heavy chain

<400> SEQUENCE: 64

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ile Thr Ser Gly
            20                  25                  30

Tyr Trp Asp Trp Ile Arg Gln Pro Pro Gly Lys Gly Leu Glu Trp Ile
            35                  40                  45

Gly Tyr Ile Ser Tyr Ser Gly Ser Thr Tyr Tyr Ser Pro Ser Leu Lys
        50                  55                  60
```

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Pro Pro Gly Tyr Tyr Gly Phe Gly Pro Tyr Ala Leu Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
210                 215                 220

Gly Pro Pro Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

<210> SEQ ID NO 65
<211> LENGTH: 213
<212> TYPE: PRT
<213> ORGANISM: Artificial sequence
<220> FEATURE:
<223> OTHER INFORMATION: Synthetic sequence: Humanized monoclonal antibody light chain

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Ser Tyr Ile
            20                  25                  30

His Trp Tyr Gln Gln Lys Pro Gly Lys Ala Pro Lys Leu Leu Ile Tyr
        35                  40                  45

Thr Thr Ser Tyr Leu Ala His Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Arg Ser Thr Leu Pro Pro Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 66
<211> LENGTH: 448
<212> TYPE: PRT
<213> ORGANISM: Artificial sequence
<220> FEATURE:
<223> OTHER INFORMATION: Synthetic sequence: Humanized monoclonal
      antibody heavy chain

<400> SEQUENCE: 66

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Asp Ile Thr Ser Gly
            20                  25                  30

Tyr His Asp Trp Ile Arg Gln Pro Pro Gly Lys Gly Leu Glu Trp Ile
        35                  40                  45

Gly Tyr Ile Ser Tyr Ser Gly Ser Thr Tyr Tyr Ser Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Pro Pro Gly Tyr Tyr Gly Phe Gly Pro Tyr Ala Leu Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
                260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
                420                 425                 430

Ala Leu His Asn His Tyr Thr Gln Lys Ser Leu Ser Leu Ser Leu Gly
            435                 440                 445

<210> SEQ ID NO 67
<211> LENGTH: 448
<212> TYPE: PRT
<213> ORGANISM: Artificial sequence
<220> FEATURE:
<223> OTHER INFORMATION: Synthetic sequence: Humanized monoclonal
      antibody heavy chain

<400> SEQUENCE: 67

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Asp Ile Thr Ser Gly
            20                  25                  30

Tyr His Asp Trp Ile Arg Gln Pro Pro Gly Lys Gly Leu Glu Trp Ile
        35                  40                  45

-continued

Gly Tyr Ile Ser Tyr Ser Gly Ser Thr Gln Tyr Ser Pro Ser Leu Lys
    50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Pro Pro Gly Tyr Tyr Gly Phe Gly Pro Tyr Ala Leu Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

<210> SEQ ID NO 68
<211> LENGTH: 448
<212> TYPE: PRT

<213> ORGANISM: Artificial sequence
<220> FEATURE:
<223> OTHER INFORMATION: Synthetic sequence: Humanized monoclonal antibody heavy chain

<400> SEQUENCE: 68

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Asp Ile Thr Ser Gly
            20                  25                  30

Tyr His Asp Trp Ile Arg Gln Pro Pro Gly Lys Gly Leu Glu Trp Ile
        35                  40                  45

Gly Tyr Ile Ser Tyr Ser Gly Ser Thr Tyr Tyr Ser Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Pro Pro Ala Tyr Tyr Gly Phe Gly Pro Tyr Ala Leu Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu

```
            385                 390                 395                 400
Asp Ser Asp Gly Ser Phe Phe Leu Tyr Ser Arg Leu Thr Val Asp Lys
                    405                 410                 415

Ser Arg Trp Gln Glu Gly Asn Val Phe Ser Cys Ser Val Met His Glu
                420                 425                 430

Ala Leu His Asn His Tyr Thr Gln Lys Ser Leu Ser Leu Ser Leu Gly
            435                 440                 445

<210> SEQ ID NO 69
<211> LENGTH: 448
<212> TYPE: PRT
<213> ORGANISM: Artificial sequence
<220> FEATURE:
<223> OTHER INFORMATION: Synthetic sequence: Humanized monoclonal
      antibody heavy chain

<400> SEQUENCE: 69

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Asp Ile Thr Ser Gly
            20                  25                  30

Tyr His Glu Trp Ile Arg Gln Pro Pro Gly Lys Gly Leu Glu Trp Ile
        35                  40                  45

Gly Tyr Ile Ser Tyr Ser Gly Ser Thr Ser Tyr Ser Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Pro Pro Ala Tyr Tyr Gly Phe Gly Pro Tyr Ala Leu Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
```

```
                305                 310                 315                 320
Tyr Lys Cys Lys Val Ser Asn Lys Gly Leu Pro Ser Ser Ile Glu Lys
                    325                 330                 335
Thr Ile Ser Lys Ala Lys Gly Gln Pro Arg Glu Pro Gln Val Tyr Thr
                340                 345                 350
Leu Pro Pro Ser Gln Glu Glu Met Thr Lys Asn Gln Val Ser Leu Thr
            355                 360                 365
Cys Leu Val Lys Gly Phe Tyr Pro Ser Asp Ile Ala Val Glu Trp Glu
        370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Arg Leu Thr Val Asp Lys
                405                 410                 415
Ser Arg Trp Gln Glu Gly Asn Val Phe Ser Cys Ser Val Met His Glu
            420                 425                 430
Ala Leu His Asn His Tyr Thr Gln Lys Ser Leu Ser Leu Ser Leu Gly
        435                 440                 445
```

<210> SEQ ID NO 70
<211> LENGTH: 639
<212> TYPE: DNA
<213> ORGANISM: Artificial sequence
<220> FEATURE:
<223> OTHER INFORMATION: Synthetic sequence: DNA sequence encoding the
      humanized monoclonal antibody light chain of SEQ ID NO: 59

<400> SEQUENCE: 70

```
gatattcaga tgacccagag cccgagcagc ctgagcgcga gcgtgggcga tcgcgtgacc      60
attacctgca gcgcgagcag cagcgtgagc tatatgcatt ggtatcagca gaaaccgggc     120
aaagcgccga aactgctgat ttataccacc agcaacctgg cgcatggcgt gccgagccgc     180
tttagcggca gcggcagcgg caccgatttt accctgacca ttagcagcct gcagccggaa     240
gattttgcga cctattattg ccagtggcgc agcaccctgc cgccgacctt tggcggcggc     300
accaaagtgg aaattaaacg caccgtggcg gcgccgagcg tgtttatttt tccgccgagc     360
gatgaacagc tgaaaagcgg caccgcgagc gtggtgtgcc tgctgaacaa cttttatccg     420
cgcgaagcga agtgcagtg gaaagtggat aacgcgctgc agagcggcaa cagccaggaa     480
agcgtgaccg aacaggatag caaagatagc acctatagcc tgagcagcac cctgaccctg     540
agcaaagcgg attatgaaaa acataaagtg tatgcgtgcg aagtgaccca tcagggcctg     600
agcagcccgg tgaccaaaag ctttaaccgc ggcgaatgc                            639
```

<210> SEQ ID NO 71
<211> LENGTH: 1344
<212> TYPE: DNA
<213> ORGANISM: Artificial sequence
<220> FEATURE:
<223> OTHER INFORMATION: Synthetic sequence: DNA sequence encoding the
      humanized monoclonal antibody heavy chain of SEQ ID NO: 60

<400> SEQUENCE: 71

```
caggtgcagc tgcaggaaag cggcccgggc ctggtgaaac cgagcgaaac cctgagcctg      60
acctgcaccg tgagcggcga tgatattacc agcggctatt gggattggat tcgccagccg     120
ccgggcaaag gcctggaatg gattggctat attagctata gcggcagcac ctattatagc     180
ccgagcctga aaagccgcgt gaccattagc gtggatacca gcaaaaacca gtttagcctg     240
aaactgagca gcgtgaccgc ggcggatacc gcggtgtatt attgcgcgcg cccgccgggc     300
```

```
tattatggct ttggcccgta tgcgctggat tattggggcc agggcaccct ggtgaccgtg      360
agcagcgcga gcaccaaagg cccgagcgtg tttccgctgg cgccgtgcag ccgcagcacc      420
agcgaaagca ccgcggcgct gggctgcctg gtgaaagatt attttccgga accggtgacc      480
gtgagctgga acagcggcgc gctgaccagc ggcgtgcata cctttccggc ggtgctgcag      540
agcagcggcc tgtatagcct gagcagcgtg gtgaccgtgc cgagcagcag cctgggcacc      600
aaaacctata cctgcaacgt ggatcataaa ccgagcaaca ccaaagtgga taaacgcgtg      660
gaaagcaaat atggcccgcc gtgcccgccg tgcccggcgc cggaagcggc gggcggcccg      720
agcgtgtttc tgtttccgcc gaaaccgaaa gataccctga tgattagccg cacccccgga    780
gtgacctgcg tggtggtgga tgtgagccag gaagatccgg aagtgcagtt taactggtat      840
gtggatggcg tggaagtgca taacgcgaaa accaaaccgc gcgaagaaca gtttaacagc      900
acctatcgcg tggtgagcgt gctgaccgtg ctgcatcagg attggctgaa cggcaaagaa      960
tataaatgca agtgagcaa caaaggcctg ccgagcagca ttgaaaaaac cattagcaaa     1020
gcgaaaggcc agccgcgcga accgcaggtg tatacctgc cgccgagcca ggaagaaatg      1080
accaaaaacc aggtgagcct gacctgcctg gtgaaaggct tttatccgag cgatattgcg      1140
gtggaatggg aaagcaacgg ccagccggaa aacaactata aaccaccccc gccggtgctg      1200
gatagcgatg gcagcttttt tctgtatagc cgcctgaccg tggataaaag ccgctggcag      1260
gaaggcaacg tgtttagctg cagcgtgatg catgaagcgc tgcataacca ttatacccag      1320
aaaagcctga gcctgagcct gggc                                            1344

<210> SEQ ID NO 72
<211> LENGTH: 639
<212> TYPE: DNA
<213> ORGANISM: Artificial sequence
<220> FEATURE:
<223> OTHER INFORMATION: Synthetic sequence: DNA sequence encoding the
      humanized monoclonal antibody light chain of SEQ ID NO: 61

<400> SEQUENCE: 72
gatattcaga tgacccagag cccgagcagc ctgagcgcga gcgtgggcga tcgcgtgacc       60
attacctgca gctatagcag cagcgtgagc tatatgcatt ggtatcagca gaaaccgggc      120
aaagcgccga aactgctgat ttataccacc agcaacctgg cgcatggcgt gccgagccgc      180
tttagcggca gcggcagcgg caccgatttt accctgacca ttagcagcct gcagccggaa      240
gattttgcga cctattattg ccagcagcgc agcaccctgc cgccgaccttt ggcggcggc      300 accaaagtgg aaattaaacg caccgtggcg gcgccgagcg tgtttatttt tccgccgagc      360
gatgaacagc tgaaaagcgg caccgcgagc gtggtgtgcc tgctgaacaa cttttatccg      420
cgcgaagcga aagtgcagtg gaaagtggat aacgcgctgc agagcggcaa cagccaggaa      480
agcgtgaccg aacaggatag caaagatagc acctatagcc tgagcagcac cctgaccctg      540
agcaaagcgg attatgaaaa acataaagtg tatgcgtgcg aagtgaccca tcagggcctg      600
agcagcccgg tgaccaaaag ctttaaccgc ggcgaatgc                             639

<210> SEQ ID NO 73
<211> LENGTH: 1344
<212> TYPE: DNA
<213> ORGANISM: Artificial sequence
<220> FEATURE:
<223> OTHER INFORMATION: Synthetic sequence: DNA sequence encoding the
      humanized monoclonal antibody heavy chain of SEQ ID NO: 62

<400> SEQUENCE: 73
```

```
caggtgcagc tgcaggaaag cggcccgggc ctggtgaaac cgagcgaaac cctgagcctg      60
acctgcaccg tgagcggcga tgatattacc agcggctatt ggaactggat tcgccagccg     120
ccgggcaaag gcctggaatg gattggctat attagctata gcggcagcac ctattatatt     180
ccgagcctga aaagccgcgt gaccattagc gtggatacca gcaaaaacca gtttagcctg     240
aaactgagca gcgtgaccgc ggcggatacc gcggtgtatt attgcgcgcg cccgccgggc     300
tattatggct ttggcccgta tgcgatggat tattggggcc agggcacccc tggtgaccgtg     360
agcagcgcga gcaccaaagg cccgagcgtg tttccgctgg cgccgtgcag ccgcagcacc     420
agcgaaagca ccgcggcgct gggctgcctg gtgaaagatt attttccgga accggtgacc     480
gtgagctgga acagcggcgc gctgaccagc ggcgtgcata cctttccggc ggtgctgcag     540
agcagcggcc tgtatagcct gagcagcgtg gtgaccgtgc cgagcagcag cctgggcacc     600
aaaacctata cctgcaacgt ggatcataaa ccgagcaaca ccaaagtgga taaacgcgtg     660
gaaagcaaat atggcccgcc gtgcccgccg tgcccggcgc cggaagcggc gggcggcccg     720
agcgtgtttc tgtttccgcc gaaaccgaaa gataccctga tgattagccg caccccggaa     780
gtgacctgcg tggtggtgga tgtgagccag gaagatccgg aagtgcagtt taactggtat     840
gtggatggcg tggaagtgca taacgcgaaa accaaaccgc gcgaagaaca gtttaacagc     900
acctatcgcg tggtgagcgt gctgaccgtg ctgcatcagg attggctgaa cggcaaagaa     960
tataaatgca aagtgagcaa caaaggcctg ccgagcagca ttgaaaaaac cattagcaaa    1020
gcgaaaggcc agccgcgcga accgcaggtg tataccctgc cgccgagcca ggaagaaatg    1080
accaaaaacc aggtgagcct gacctgcctg gtgaaaggct tttatccgag cgatattgcg    1140
gtggaatggg aaagcaacgg ccagccggaa aacaactata aaaccacccc gccggtgctg    1200
gatagcgatg gcagcttttt tctgtatagc cgcctgaccg tggataaaag ccgctggcag    1260
gaaggcaacg tgtttagctg cagcgtgatg catgaagcgc tgcataacca ttatacccag    1320
aaaagcctga gcctgagcct gggc                                           1344
```

<210> SEQ ID NO 74
<211> LENGTH: 639
<212> TYPE: DNA
<213> ORGANISM: Artificial sequence
<220> FEATURE:
<223> OTHER INFORMATION: Synthetic sequence: DNA sequence encoding the humanized monoclonal antibody light chain of SEQ ID NO: 63

<400> SEQUENCE: 74

```
gatattcaga tgacccagag cccgagcagc ctgagcgcga gcgtgggcga tcgcgtgacc      60
attacctgca gcgcgagcag cagcgtgagc tatattcatt ggtatcagca gaaaccgggc     120
aaagcgccga aactgctgat ttataccacc agctatctgg cgcatggcgt gccgagccgc     180
tttagcggca gcggcagcgg caccgatttt accctgacca ttagcagcct gcagccggaa     240
gattttgcga cctattattg cctgcagcgc agcaccctgc cgccgacctt tggcggcggc     300
accaaagtgg aaattaaacg cacccgtggcg gcgccgagcg tgtttatttt tccgccgagc     360
gatgaacagc tgaaaagcgg caccgcgagc gtggtgtgcc tgctgaacaa cttttatccg     420
cgcgaagcga agtgcagtg gaaagtggat aacgcgctgc agagcggcaa cagccaggaa     480
agcgtgaccg aacaggatag caaagatagc acctatagcc tgagcagcac cctgaccctg     540
agcaaagcgg attatgaaaa acataaagtg tatgcgtgcg aagtgaccca tcagggcctg     600
agcagccccg tgaccaaaag ctttaaccgc ggcgaatgc                            639
```

<210> SEQ ID NO 75
<211> LENGTH: 1344
<212> TYPE: DNA
<213> ORGANISM: Artificial sequence
<220> FEATURE:
<223> OTHER INFORMATION: Synthetic sequence: DNA sequence encoding the humanized monoclonal antibody heavy chain of SEQ ID NO: 64

<400> SEQUENCE: 75

```
caggtgcagc tgcaggaaag cggcccgggc ctggtgaaac cgagcgaaac cctgagcctg      60
acctgcaccg tgagcggcga tgatattacc agcggctatt gggattggat tcgccagccg     120
ccgggcaaag cctggaatg gattggctat attagctata gcggcagcac ctattatagc      180
ccgagcctga aaagccgcgt gaccattagc gtggatacca gcaaaaacca gtttagcctg     240
aaactgagca gcgtgaccgc ggcggatacc gcggtgtatt attgcgcgcg cccgccgggc     300
tattatggct ttggcccgta tgcgctggat tattggggcc agggcaccct ggtgaccgtg     360
agcagcgcga gcaccaaagg cccgagcgtg tttccgctgg cgccgtgcag ccgcagcacc     420
agcgaaagca ccgcggcgct gggctgcctg gtgaaagatt attttccgga accggtgacc     480
gtgagctgga acagcggcgc gctgaccagc ggcgtgcata cctttccggc ggtgctgcag     540
agcagcggcc tgtatagcct gagcagcgtg gtgaccgtgc cgagcagcag cctgggcacc     600
aaaacctata cctgcaacgt ggatcataaa ccgagcaaca ccaaagtgga taaacgcgtg     660
gaaagcaaat atggcccgcc gtgcccgccg tgcccggcgc cggaagcggc gggcggcccg     720
agcgtgtttc tgtttccgcc gaaaccgaaa gataccctga tgattagccg caccccggaa     780
gtgacctgcg tggtggtgga tgtgagccag gaagatccgg aagtgcagtt taactggtat     840
gtggatggcg tggaagtgca taacgcgaaa accaaaccgc gcgaagaaca gtttaacagc     900
acctatcgcg tggtgagcgt gctgaccgtg ctgcatcagg attggctgaa cggcaaagaa     960
tataaatgca agtgagcaa caaaggcctg ccgagcagca ttgaaaaaac cattagcaaa    1020
gcgaaaggcc agccgcgcga accgcaggtg tatacectge cgccgagcca ggaagaaatg    1080
accaaaaacc aggtgagcct gacctgcctg gtgaaaggct tttatccgag cgatattgcg    1140
gtggaatggg aaagcaacgg ccagccggaa aacaactata aaaccacccc gccggtgctg    1200
gatagcgatg gcagcttttt tctgtatagc cgcctgaccg tggataaaag ccgctggcag    1260
gaaggcaacg tgtttagctg cagcgtgatg catgaagcgc tgcataacca ttatacccag    1320
aaaagcctga gcctgagcct gggc                                          1344
```

<210> SEQ ID NO 76
<211> LENGTH: 639
<212> TYPE: DNA
<213> ORGANISM: Artificial sequence
<220> FEATURE:
<223> OTHER INFORMATION: Synthetic sequence: DNA sequence encoding the humanized monoclonal antibody light chain of SEQ ID NO: 65

<400> SEQUENCE: 76

```
gatattcaga tgacccagag cccgagcagc ctgagcgcga gcgtgggcga tcgcgtgacc      60
attacctgca gcgcgagcag cagcgtgagc tatattcatt ggtatcagca gaaaccgggc     120
aaagcgccga aactgctgat ttataccacc agctatctgg cgcatggcgt gccgagccgc     180
tttagcggca gcggcagcgg caccgatttt accctgacca ttagcagcct gcagccggaa     240
gattttgcga cctattattg ccagcagcgc agcaccctgc cgccgacctt tggcggcggc     300
accaaagtgg aaattaaacg cacegtggeg gcgccgagcg tgtttatttt ccgccgagc     360
gatgaacagc tgaaaagcgg caccgcgagc gtggtgtgcc tgctgaacaa cttttatccg     420
```

| | |
|---|---|
| cgcgaagcga aagtgcagtg gaaagtggat aacgcgctgc agagcggcaa cagccaggaa | 480 |
| agcgtgaccg aacaggatag caaagatagc acctatagcc tgagcagcac cctgaccctg | 540 |
| agcaaagcgg attatgaaaa acataaagtg tatgcgtgcg aagtgaccca tcagggcctg | 600 |
| agcagcccgg tgaccaaaag ctttaaccgc ggcgaatgc | 639 |

<210> SEQ ID NO 77
<211> LENGTH: 1344
<212> TYPE: DNA
<213> ORGANISM: Artificial sequence
<220> FEATURE:
<223> OTHER INFORMATION: Synthetic sequence: DNA sequence encoding the humanized monoclonal antibody heavy chain of SEQ ID NO: 66

<400> SEQUENCE: 77

| | |
|---|---|
| caggtgcagc tgcaggaaag cggcccgggc ctggtgaaac cgagcgaaac cctgagcctg | 60 |
| acctgcaccg tgagcggcga tgatattacc agcggctatc atgattggat tcgccagccg | 120 |
| ccgggcaaag gcctggaatg gattggctat attagctata gcggcagcac ctattatagc | 180 |
| ccgagcctga aaagccgcgt gaccattagc gtggatacca gcaaaaacca gtttagcctg | 240 |
| aaactgagca gcgtgaccgc ggcggatacc gcggtgtatt attgcgcgcg cccgccgggc | 300 |
| tattatggct ttggcccgta tgcgctggat tattggggcc agggcaccct ggtgaccgtg | 360 |
| agcagcgcga gcaccaaagg cccgagcgtg tttccgctgg cgccgtgcag ccgcagcacc | 420 |
| agcgaaagca cccgcgcgct gggctgcctg gtgaaagatt attttccgga accggtgacc | 480 |
| gtgagctgga acagcggcgc gctgaccagc ggcgtgcata ccttccggc ggtgctgcag | 540 |
| agcagcggcc tgtatagcct gagcagcgtg gtgaccgtgc cgagcagcag cctgggcacc | 600 |
| aaaacctata cctgcaacgt ggatcataaa ccgagcaaca ccaaagtgga taaacgcgtg | 660 |
| gaaagcaaat atggcccgcc gtgcccgccc tgcccggcgc cggaagcggc gggcggcccg | 720 |
| agcgtgtttc tgtttccgcc gaaaccgaaa gataccctga tgattagccg cacccccgaa | 780 |
| gtgacctgcg tggtggtgga tgtgagccag gaagatccgg aagtgcagtt taactggtat | 840 |
| gtggatggcg tggaagtgca taacgcgaaa accaaaccgc gcgaagaaca gtttaacagc | 900 |
| acctatcgcg tggtgagcgt gctgaccgtg ctgcatcagg attggctgaa cggcaaagaa | 960 |
| tataaatgca aagtgagcaa caaaggcctg ccgagcagca ttgaaaaaac cattagcaaa | 1020 |
| gcgaaaggcc agccgcgcga accgcaggtg tatacc ctgc cgccagcca ggaagaaatg | 1080 |
| accaaaaacc aggtgagcct gacctgcctg gtgaaaggct tttatccgag cgatattgcg | 1140 |
| gtggaatggg aaagcaacgg ccagccggaa aacaactata aaccaccccc ggcggtgctg | 1200 |
| gatagcgatg gcagcttttt tctgtatagc cgcctgaccg tggataaaag ccgctggcag | 1260 |
| gaaggcaacg tgtttagctg cagcgtgatg catgaagcgc tgcataacca ttatacccag | 1320 |
| aaaagcctga gcctgagcct gggc | 1344 |

<210> SEQ ID NO 78
<211> LENGTH: 1344
<212> TYPE: DNA
<213> ORGANISM: Artificial sequence
<220> FEATURE:
<223> OTHER INFORMATION: Synthetic sequence: DNA sequence encoding the humanized monoclonal antibody heavy chain of SEQ ID NO: 67

<400> SEQUENCE: 78

| | |
|---|---|
| caggtgcagc tgcaggaaag cggcccgggc ctggtgaaac cgagcgaaac cctgagcctg | 60 |
| acctgcaccg tgagcggcga tgatattacc agcggctatc atgattggat tcgccagccg | 120 |

```
ccgggcaaag gcctggaatg gattggctat attagctata gcggcagcac ccagtatagc    180
ccgagcctga aaagccgcgt gaccattagc gtggatacca gcaaaaacca gtttagcctg    240
aaactgagca gcgtgaccgc ggcggatacc gcggtgtatt attgcgcgcg cccgccgggc    300
tattatggct ttggcccgta tgcgctggat tattggggcc agggcaccct ggtgaccgtg    360
agcagcgcga gcaccaaagg cccgagcgtg tttccgctgg cgccgtgcag ccgcagcacc    420
agcgaaagca ccgcggcgct gggctgcctg gtgaaagatt attttccgga accggtgacc    480
gtgagctgga acagcggcgc gctgaccagc ggcgtgcata cctttccggc ggtgctgcag    540
agcagcggcc tgtatagcct gagcagcgtg gtgaccgtgc cgagcagcag cctgggcacc    600
aaaacctata cctgcaacgt ggatcataaa ccgagcaaca ccaaagtgga taaacgcgtg    660
gaaagcaaat atggcccgcc gtgcccgccg tgcccggcgc cggaagcggc gggcggcccg    720
agcgtgtttc tgtttccgcc gaaaccgaaa gatacccctga tgattagccg cacccccggaa    780 gtgacctgcg tggtggtgga tgtgagccag gaagatccgg aagtgcagtt taactggtat    840
gtggatggcg tggaagtgca taacgcgaaa accaaaccgc gcgaagaaca gtttaacagc    900
acctatcgcg tggtgagcgt gctgaccgtg ctgcatcagg attggctgaa cggcaaagaa    960
tataaatgca aagtgagcaa caaaggcctg ccgagcagca ttgaaaaaac cattagcaaa    1020
gcgaaaggcc agccgcgcga accgcaggtg tatacccctgc cgccgagcca ggaagaaatg    1080
accaaaaacc aggtgagcct gacctgcctg gtgaaaggct tttatccgag cgatattgcg    1140
gtggaatggg aaagcaacgg ccagccggaa aacaactata aaaccacccc gccggtgctg    1200
gatagcgatg gcagctttt tctgtatagc cgcctgaccg tggataaaag ccgctggcag    1260
gaaggcaacg tgtttagctg cagcgtgatg catgaagcgc tgcataacca ttatacccag    1320
aaaagcctga gcctgagcct gggc    1344
```

<210> SEQ ID NO 79
<211> LENGTH: 1344
<212> TYPE: DNA
<213> ORGANISM: Artificial sequence
<220> FEATURE:
<223> OTHER INFORMATION: Synthetic sequence: DNA sequence encoding the
      humanized monoclonal antibody heavy chain of SEQ ID NO: 68

<400> SEQUENCE: 79

```
caggtgcagc tgcaggaaag cggcccgggc ctggtgaaac cgagcgaaac cctgagcctg     60
acctgcaccg tgagcggcga tgatattacc agcggctatc atgattggat tcgccagccg    120
ccgggcaaag gcctggaatg gattggctat attagctata gcggcagcac ctattatagc    180
ccgagcctga aaagccgcgt gaccattagc gtggatacca gcaaaaacca gtttagcctg    240
aaactgagca gcgtgaccgc ggcggatacc gcggtgtatt attgcgcgcg cccgccggcg    300
tattatggct ttggcccgta tgcgctggat tattggggcc agggcaccct ggtgaccgtg    360
agcagcgcga gcaccaaagg cccgagcgtg tttccgctgg cgccgtgcag ccgcagcacc    420
agcgaaagca ccgcggcgct gggctgcctg gtgaaagatt attttccgga accggtgacc    480
gtgagctgga acagcggcgc gctgaccagc ggcgtgcata cctttccggc ggtgctgcag    540
agcagcggcc tgtatagcct gagcagcgtg gtgaccgtgc cgagcagcag cctgggcacc    600
aaaacctata cctgcaacgt ggatcataaa ccgagcaaca ccaaagtgga taaacgcgtg    660
gaaagcaaat atggcccgcc gtgcccgccg tgcccggcgc cggaagcggc gggcggcccg    720
agcgtgtttc tgtttccgcc gaaaccgaaa gatacccctga tgattagccg cacccccggaa    780
```

```
gtgacctgcg tggtggtgga tgtgagccag aagatccgg  aagtgcagtt taactggtat      840
gtggatggcg tggaagtgca taacgcgaaa accaaaccgc gcgaagaaca gtttaacagc      900
acctatcgcg tggtgagcgt gctgaccgtg ctgcatcagg attggctgaa cggcaaagaa      960
tataaatgca aagtgagcaa caaaggcctg ccgagcagca ttgaaaaaac cattagcaaa     1020
gcgaaaggcc agccgcgcga accgcaggtg tataccctgc cgccgagcca ggaagaaatg     1080
accaaaaacc aggtgagcct gacctgcctg gtgaaaggct tttatccgag cgatattgcg     1140
gtggaatggg aaagcaacgg ccagccggaa aacaactata aaccaccccc gccggtgctg     1200
gatagcgatg gcagctttt  tctgtatagc cgcctgaccg tggataaaag ccgctggcag     1260
gaaggcaacg tgtttagctg cagcgtgatg catgaagcgc tgcataacca ttatacccag     1320
aaaagcctga gcctgagcct gggc                                            1344

<210> SEQ ID NO 80
<211> LENGTH: 1344
<212> TYPE: DNA
<213> ORGANISM: Artificial sequence
<220> FEATURE:
<223> OTHER INFORMATION: Synthetic sequence: DNA sequence encoding the
      humanized monoclonal antibody heavy chain of SEQ ID NO: 69

<400> SEQUENCE: 80
caggtgcagc tgcaggaaag cggcccgggc ctggtgaaac cgagcgaaac cctgagcctg       60
acctgcaccg tgagcggcga tgatattacc agcggctatc atgaatggat tcgccagccg      120
ccgggcaaag cctggaatg  gattggctat attagctata gcggcagcac cagctatagc      180
ccgagcctga aaagccgcgt gaccattagc gtggatacca gcaaaaacca gtttagcctg      240
aaactgagca gcgtgaccgc ggcggatacc gcggtgtatt attgcgcgcg cccgccggcg      300
tattatggct ttggcccgta tgcgctggat tattggggcc agggcacccc tggtgaccgtg      360 agcagcgcga gcaccaaagg cccgagcgtg tttccgctgg cgccgtgcag ccgcagcacc      420
agcgaaagca ccgcggcgct gggctgcctg gtgaaagatt attttccgga accggtgacc      480
gtgagctgga acagcggcgc gctgaccagc ggcgtgcata ccttccggc  ggtgctgcag      540 agcagcggcc tgtatagcct gagcagcgtg gtgaccgtgc cgagcagcag cctgggcacc      600
aaaacctata cctgcaacgt ggatcataaa ccgagcaaca ccaaagtgga taaacgcgtg      660
gaaagcaaat atggcccgcc gtgcccgccg tgcccggcgc cggaagcggc gggcggcccg      720
agcgtgtttc tgtttccgcc gaaaccgaaa gataccctga tgattagccg cacccccgaa      780
gtgacctgcg tggtggtgga tgtgagccag aagatccgg  aagtgcagtt taactggtat      840
gtggatggcg tggaagtgca taacgcgaaa accaaaccgc gcgaagaaca gtttaacagc      900
acctatcgcg tggtgagcgt gctgaccgtg ctgcatcagg attggctgaa cggcaaagaa      960
tataaatgca aagtgagcaa caaaggcctg ccgagcagca ttgaaaaaac cattagcaaa     1020
gcgaaaggcc agccgcgcga accgcaggtg tataccctgc cgccgagcca ggaagaaatg     1080
accaaaaacc aggtgagcct gacctgcctg gtgaaaggct tttatccgag cgatattgcg     1140
gtggaatggg aaagcaacgg ccagccggaa aacaactata aaccaccccc gccggtgctg     1200
gatagcgatg gcagctttt  tctgtatagc cgcctgaccg tggataaaag ccgctggcag     1260
gaaggcaacg tgtttagctg cagcgtgatg catgaagcgc tgcataacca ttatacccag     1320
aaaagcctga gcctgagcct gggc                                            1344
```